(12) United States Patent
Datta et al.

(10) Patent No.: US 7,473,818 B2
(45) Date of Patent: Jan. 6, 2009

(54) PRODUCT SEAL OF DISSIMILAR MATERIALS

(75) Inventors: Paul J. Datta, Appleton, WI (US);
Kristi Jo Bryant, Appleton, WI (US);
Timothy J. Blenke, Neenah, WI (US);
Stephen C. Baumgartner, Neenah, WI (US); Julie A. Moser, Lawrenceburg, IN (US); Barbara A. Gossen, Oshkosh, WI (US); Catherine Marguerite Hancock-Cook, Neenah, WI (US);
Mark G. Everson, Neenah, WI (US);
Peter S. Lortscher, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1244 days.

(21) Appl. No.: 10/010,965

(22) Filed: Dec. 7, 2001

(65) Prior Publication Data
US 2002/0165514 A1 Nov. 7, 2002

Related U.S. Application Data

(60) Provisional application No. 60/272,548, filed on Mar. 1, 2001.

(51) Int. Cl.
*A61F 13/49* (2006.01)
*A61F 13/56* (2006.01)

(52) U.S. Cl. ............ 604/366; 604/367; 604/370; 604/372; 604/385.11; 604/389

(58) Field of Classification Search ................ 604/365, 604/366, 367, 376, 385, 385.01, 385.11, 604/385.24, 385.31, 386, 389, 391, 392–396
See application file for complete search history.

(56) References Cited

U.S. PATENT DOCUMENTS

| 4,443,513 | A |   | 4/1984  | Meitner et al. |
|-----------|---|---|---------|----------------|
| 4,663,220 | A |   | 5/1987  | Wisneski et al. |
| D290,780  | S |   | 7/1987  | Wistrand |
| 4,704,116 | A |   | 11/1987 | Enloe |
| 4,798,603 | A |   | 1/1989  | Meyer et al. |
| 4,965,122 | A |   | 10/1990 | Morman |
| 4,981,747 | A |   | 1/1991  | Morman |
| 5,032,450 | A |   | 7/1991  | Rechlicz et al. |
| 5,061,261 | A |   | 10/1991 | Suzuki et al. |
| 5,074,854 | A | * | 12/1991 | Davis ................ 604/385.11 |

(Continued)

FOREIGN PATENT DOCUMENTS

EP 0 217 032 4/1987

(Continued)

*Primary Examiner*—Karin M Reichle
(74) *Attorney, Agent, or Firm*—Armstrong Teasdale

(57) ABSTRACT

A pant-like, prefastened, disposable absorbent article having side seams which include a front ear passively bonded to a back ear, wherein the front ear is releasable from the back ear desirably without tearing or damaging the back ear. The tearable front ear has a basis weight less than a basis weight of the back ear.

16 Claims, 14 Drawing Sheets

U.S. PATENT DOCUMENTS

| | | | |
|---|---|---|---|
| 5,106,385 A | 4/1992 | Allen et al. | |
| 5,114,781 A | 5/1992 | Morman | |
| 5,116,662 A | 5/1992 | Morman | |
| 5,151,092 A | 9/1992 | Buell et al. | |
| 5,163,932 A | 11/1992 | Nomura et al. | |
| 5,169,712 A | 12/1992 | Tapp | |
| 5,176,668 A | 1/1993 | Bernardin | |
| 5,176,671 A | 1/1993 | Roessler et al. | |
| 5,176,672 A | 1/1993 | Bruemmer et al. | |
| 5,192,606 A | 3/1993 | Proxmire et al. | |
| 5,196,000 A | 3/1993 | Clear et al. | |
| 5,208,098 A | 5/1993 | Stover | |
| 5,221,274 A | 6/1993 | Buell et al. | |
| 5,226,992 A | 7/1993 | Morman | |
| 5,234,423 A | 8/1993 | Alemany et al. | |
| 5,238,733 A | 8/1993 | Joseph et al. | |
| 5,242,436 A | 9/1993 | Weil et al. | |
| 5,244,482 A | 9/1993 | Hassenboehler, Jr. et al. | |
| D341,197 S | 11/1993 | Patterson | |
| D342,786 S | 12/1993 | De Gooijer | |
| D343,681 S | 1/1994 | Hull | |
| 5,294,478 A | 3/1994 | Wanek et al. | |
| 5,304,161 A | 4/1994 | Noel et al. | |
| 5,312,387 A | 5/1994 | Rossini et al. | |
| 5,320,891 A | 6/1994 | Levy et al. | |
| 5,336,545 A | 8/1994 | Morman | |
| 5,358,500 A | 10/1994 | Lavon et al. | |
| 5,366,451 A | 11/1994 | Levesque | |
| 5,368,584 A | 11/1994 | Clear et al. | |
| 5,370,634 A | 12/1994 | Ando et al. | |
| 5,383,871 A | 1/1995 | Carlin et al. | |
| 5,393,599 A | 2/1995 | Quantrille et al. | |
| 5,407,507 A | 4/1995 | Ball | |
| 5,409,761 A | 4/1995 | Langley | |
| H1440 H | 5/1995 | New et al. | |
| 5,413,811 A | 5/1995 | Fitting et al. | |
| D361,839 S | 8/1995 | Doss | |
| 5,439,458 A | 8/1995 | Noel et al. | |
| 5,454,803 A | 10/1995 | Sageser et al. | |
| 5,466,513 A | 11/1995 | Wanek et al. | |
| 5,482,765 A | 1/1996 | Bradley et al. | |
| 5,491,846 A * | 2/1996 | Muller | 2/400 |
| 5,492,753 A | 2/1996 | Levy et al. | |
| 5,496,298 A | 3/1996 | Kuepper et al. | |
| 5,496,429 A | 3/1996 | Hasse et al. | |
| 5,507,736 A | 4/1996 | Clear et al. | |
| 5,507,895 A | 4/1996 | Suekane | |
| 5,509,915 A | 4/1996 | Hanson et al. | |
| 5,514,470 A | 5/1996 | Haffner et al. | |
| 5,527,304 A | 6/1996 | Buell et al. | |
| 5,531,732 A | 7/1996 | Wood | |
| 5,540,976 A | 7/1996 | Shawver et al. | |
| D372,532 S | 8/1996 | Rossini et al. | |
| 5,542,942 A | 8/1996 | Kline et al. | |
| 5,542,943 A | 8/1996 | Sageser | |
| 5,545,275 A | 8/1996 | Herrin et al. | |
| 5,554,143 A | 9/1996 | Roe et al. | |
| 5,554,144 A | 9/1996 | Roe et al. | |
| 5,554,145 A | 9/1996 | Roe et al. | |
| 5,556,394 A | 9/1996 | Roe et al. | |
| 5,560,974 A | 10/1996 | Langley | |
| 5,569,232 A | 10/1996 | Roe et al. | |
| 5,571,096 A | 11/1996 | Dobrin et al. | |
| 5,575,783 A | 11/1996 | Clear et al. | |
| 5,580,411 A | 12/1996 | Nease et al. | |
| 5,582,903 A | 12/1996 | Levy et al. | |
| 5,591,152 A | 1/1997 | Buell et al. | |
| 5,595,567 A | 1/1997 | King et al. | |
| 5,599,417 A * | 2/1997 | Glaug et al. | 156/227 |
| 5,603,708 A | 2/1997 | Seth | |
| 5,618,366 A | 4/1997 | Suekane | |
| 5,622,589 A * | 4/1997 | Johnson et al. | 156/289 |
| 5,624,420 A | 4/1997 | Bridges et al. | |
| 5,626,574 A | 5/1997 | Sasaki et al. | |
| 5,628,737 A | 5/1997 | Dobrin et al. | |
| 5,634,916 A | 6/1997 | Lavon et al. | |
| 5,643,239 A | 7/1997 | Bodford et al. | |
| 5,643,242 A | 7/1997 | Lavon et al. | |
| H1674 H | 8/1997 | Ames et al. | |
| 5,653,704 A | 8/1997 | Buell et al. | |
| D383,207 S | 9/1997 | Cassell | |
| 5,662,636 A | 9/1997 | Benjamin et al. | |
| 5,669,897 A | 9/1997 | Lavon et al. | |
| 5,674,216 A | 10/1997 | Buell et al. | |
| 5,680,653 A | 10/1997 | Mathis et al. | |
| H1698 H | 11/1997 | Lloyd et al. | |
| 5,683,533 A | 11/1997 | Keighley et al. | |
| 5,690,626 A | 11/1997 | Suzuki et al. | |
| 5,690,627 A | 11/1997 | Clear et al. | |
| 5,693,038 A | 12/1997 | Suzuki et al. | |
| 5,695,849 A | 12/1997 | Shawver et al. | |
| 5,695,868 A | 12/1997 | McCormack | |
| 5,702,551 A | 12/1997 | Huber et al. | |
| D389,320 S | 1/1998 | Vinnage et al. | |
| 5,705,013 A | 1/1998 | Nease et al. | |
| 5,709,921 A | 1/1998 | Shawver | |
| 5,718,698 A | 2/1998 | Dobrin et al. | |
| 5,728,451 A | 3/1998 | Langley et al. | |
| 5,735,838 A | 4/1998 | Rönnberg et al. | |
| 5,735,840 A | 4/1998 | Kline et al. | |
| 5,749,866 A | 5/1998 | Roe et al. | |
| 5,779,691 A | 7/1998 | Schmitt | |
| 5,788,685 A | 8/1998 | Rönnberg et al. | |
| 5,788,797 A | 8/1998 | Herrin et al. | |
| 5,789,065 A | 8/1998 | Haffner et al. | |
| 5,810,797 A | 9/1998 | Menard et al. | |
| 5,817,081 A | 10/1998 | LaVon et al. | |
| 5,830,206 A * | 11/1998 | Larsson | 604/390 |
| D403,401 S | 12/1998 | Bernard et al. | |
| D403,402 S | 12/1998 | Dreier et al. | |
| D403,403 S | 12/1998 | Bernard et al. | |
| D403,404 S | 12/1998 | Bernard et al. | |
| 5,843,057 A | 12/1998 | McCormack | |
| 5,843,066 A | 12/1998 | Dobrin | |
| 5,846,232 A | 12/1998 | Serbiak et al. | |
| 5,853,881 A | 12/1998 | Estey et al. | |
| 5,855,574 A | 1/1999 | Kling et al. | |
| 5,855,999 A | 1/1999 | McCormack | |
| 5,865,823 A | 2/1999 | Curro | |
| 5,865,926 A | 2/1999 | Wu et al. | |
| 5,876,390 A | 3/1999 | Hall et al. | |
| 5,883,028 A | 3/1999 | Morman et al. | |
| 5,891,120 A | 4/1999 | Chmielewski | |
| 5,897,545 A | 4/1999 | Kline et al. | |
| 5,906,008 A | 5/1999 | Heki et al. | |
| 5,906,604 A | 5/1999 | Rönnberg et al. | |
| 5,910,225 A | 6/1999 | McAmish et al. | |
| 5,913,850 A | 6/1999 | D'Alessio et al. | |
| 5,914,084 A | 6/1999 | Benson et al. | |
| 5,916,207 A | 6/1999 | Toyoda et al. | |
| 5,921,977 A | 7/1999 | Schmitz | |
| 5,925,027 A | 7/1999 | Schmitz | |
| 5,926,926 A | 7/1999 | Kato | |
| 5,928,209 A | 7/1999 | Bodford et al. | |
| 5,931,827 A * | 8/1999 | Buell et al. | 604/385.29 |
| 5,932,497 A | 8/1999 | Morman et al. | |
| 5,938,648 A | 8/1999 | LaVon et al. | |
| 5,957,908 A | 9/1999 | Kline et al. | |
| 5,989,688 A | 11/1999 | Barge et al. | |
| 5,997,521 A | 12/1999 | Robles et al. | |
| 6,002,064 A | 12/1999 | Kobylivker et al. | |
| 6,004,306 A | 12/1999 | Robles et al. | |
| 6,015,764 A | 1/2000 | McCormack et al. | |
| 6,020,536 A | 2/2000 | Österdahl et al. | |

| | | | | | | |
|---|---|---|---|---|---|---|
| 6,022,430 | A * | 2/2000 | Blenke et al. ............... 156/73.1 | WO | 96/01094 | 1/1996 |
| 6,022,431 | A | 2/2000 | Blenke et al. | WO | 96/03101 | 2/1996 |
| 6,022,432 | A | 2/2000 | Elsberg et al. | WO | WO 96/03949 | 2/1996 |
| 6,030,372 | A | 2/2000 | Buell et al. | WO | 96/18367 | 6/1996 |
| D421,802 | S | 3/2000 | Van Gompel et al. | WO | 96/19174 | 6/1996 |
| D422,078 | S | 3/2000 | Vukos et al. | WO | 96/35402 | 11/1996 |
| 6,036,805 | A | 3/2000 | McNichols | WO | 97/23180 | 7/1997 |
| 6,050,985 | A | 4/2000 | Lavon et al. | WO | 97/25951 | 7/1997 |
| 6,051,094 | A | 4/2000 | Melbye et al. | WO | 98/05813 | 2/1998 |
| 6,086,571 | A | 7/2000 | Guevara et al. | WO | 98/29246 | 7/1998 |
| 6,113,717 | A | 9/2000 | Vogt et al. | WO | 98/29247 | 7/1998 |
| 6,132,411 | A | 10/2000 | Huber et al. | WO | 98/29479 | 7/1998 |
| 6,287,287 | B1 * | 9/2001 | Elsberg ................. 604/385.03 | WO | 98/29480 | 7/1998 |
| 6,552,245 | B1 | 4/2003 | Roessler et al. | WO | 98/35641 | 8/1998 |

FOREIGN PATENT DOCUMENTS

| | | | | | |
|---|---|---|---|---|---|
| WO | | | 98/51474 | | 11/1998 |
| WO | | | WO9853780 A1 * | | 12/1998 |
| EP | 0 235 014 B1 | 7/1991 | WO | 99/14262 | 3/1999 |
| EP | 0 233 704 B1 | 7/1992 | WO | 99/18906 | 4/1999 |
| EP | 0 400 111 B1 | 8/1994 | WO | 99/21522 | 5/1999 |
| EP | 0 691 203 A1 | 1/1996 | WO | WO 99/25296 | 5/1999 |
| EP | 0 707 106 A1 | 4/1996 | WO | 99/37263 | 7/1999 |
| EP | 0 570 980 B1 | 7/1997 | WO | 99/37839 | 7/1999 |
| EP | 0 597 331 B1 | 11/1997 | WO | 99/48452 | 9/1999 |
| EP | 0 757 550 B1 | 12/1998 | WO | 99/53881 | 10/1999 |
| EP | 0 880 856 A2 | 12/1998 | WO | WO 99/53878 | 10/1999 |
| EP | 0 587 196 B1 | 3/1999 | WO | 99/60966 | 12/1999 |
| EP | 0 734 321 B1 | 3/1999 | WO | 99/60967 | 12/1999 |
| WO | WO 83/01338 | 4/1983 | WO | 99/60968 | 12/1999 |
| WO | 94/17768 | 8/1994 | WO | 99/60972 | 12/1999 |
| WO | 94/18927 | 9/1994 | WO | 99/60973 | 12/1999 |
| WO | 94/26222 | 11/1994 | WO | 99/60974 | 12/1999 |
| WO | WO 95/06451 | 3/1995 | WO | WO 99/65438 | 12/1999 |
| WO | 95/27460 | 10/1995 | WO | 00/46023 | 8/2000 |
| WO | 95/27462 | 10/1995 | | | |
| WO | 95/27463 | 10/1995 | * cited by examiner | | |

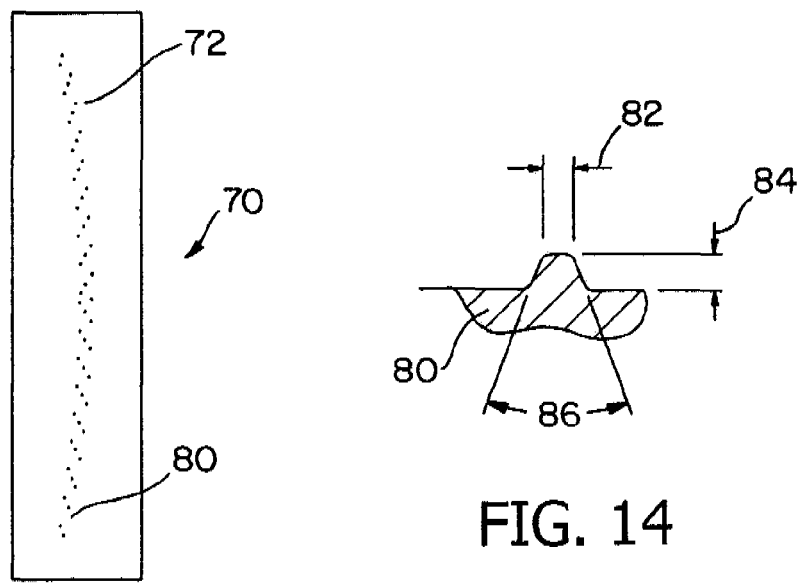
FIG. 13
FIG. 14
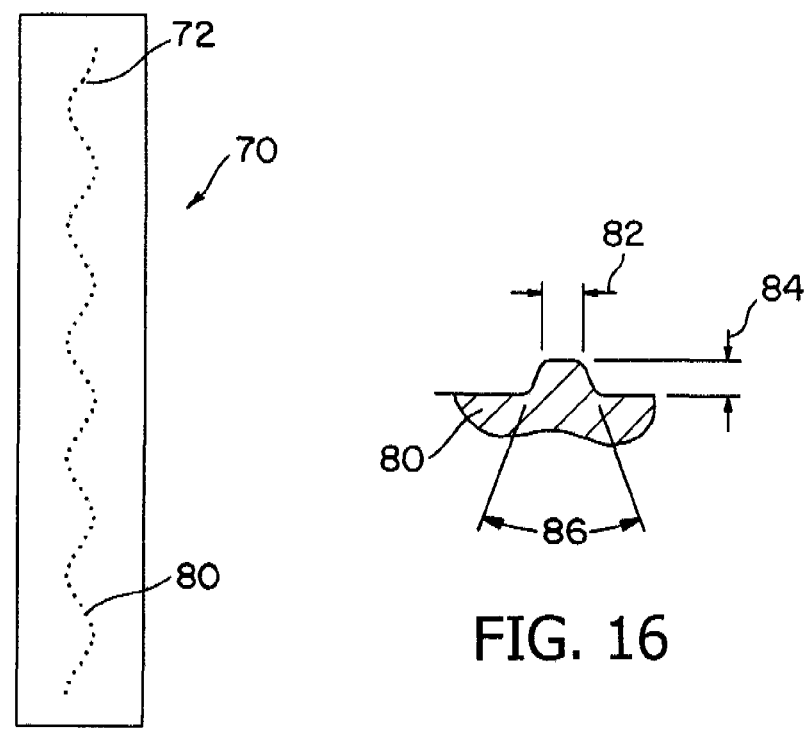
FIG. 15
FIG. 16

PRODUCT SEAL OF DISSIMILAR MATERIALS

CROSS REFERENCE TO RELATED APPLICATION

This application claims the benefit of U.S. Provisional Patent Application Ser. No. 60/272,548, filed 01 Mar. 2001.

FIELD OF INVENTION

The present invention relates to a pant-like, refastenable disposable absorbent article having side seams which include a front ear passively bonded to a back ear, wherein the front ear is releasable from the back ear desirably without tearing or damaging the back ear.

BACKGROUND OF THE INVENTION

Absorbent articles such as diapers, training pants or incontinence garments desirably provide a close, comfortable fit about the wearer and contain body exudates. Moreover, absorbent articles, after being soiled, optimally can be removed from the wearer in a convenient and clean manner without undesirably soiling the caregiver, the surrounding area or the clothes of the wearer. In certain circumstances, it is also beneficial for such absorbent articles to be capable of being pulled up or down over the hips of the wearer to allow the wearer or caregiver to easily pull the article on and easily remove the article if it has not been soiled. Given the various shapes and sizes of wearers of absorbent articles, it would also be beneficial for the caregiver or the wearer to be able to adjust the fit of the waist opening of the article.

Conventional diapers are not provided in a prefastened condition and typically include a front waist portion and a back waist portion that are releasably connected about the hips of the wearer by conventional fasteners such as adhesive tape fasteners or hook and loop fasteners. For example, conventional fasteners typically include a pair of fasteners, such as adhesive tape tabs, located on the outermost corners of the diaper in the back waist region of the diaper and a complimentary fastener, such as a taping panel, located on the exterior surface of the outer cover of the diaper in the front waist portion of the diaper. In such a configuration, the diaper is positioned between the legs of the wearer while the wearer is lying down, and the adhesive tape tabs are releasably attached to the taping panel to secure the back waist portion to the front waist portion of the diaper, to secure the diaper about the waist of the wearer. Such conventional diapers are not easily fastened about and removed from the wearer after use without undesirably soiling the caregiver. Further, such conventional diapers are not provided in a pant-like, prefastened configuration and, thus, are not configured to be pulled up or down over the hips of the wearer when the fasteners are attached. Moreover, the fasteners on such conventional diapers generally are difficult to disengage and reattach to further adjust or conform the waist opening of the diaper to the waist of the wearer. Such disengagement and reattachment can also be difficult to accomplish when the wearer is active.

Several attempts have been made to provide absorbent articles that effectively contain body exudates, are capable of being pulled up and/or down over the hips of the wearer and provide for easy cleaning and removal after being soiled. For example, some conventional absorbent articles, such as conventional training pants, include integral side panels that connect the front waist portion to the back waist portion of the absorbent article. The side panels can be made stretchable such that the waist opening of the absorbent article can expand to allow the absorbent article to be pulled up or down over the hips of the wearer if desired.

However, many of these absorbent articles have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely, which can undesirably result in leaks. As a result, many of these articles have not contained bodily exudates as effectively as conventional diaper-type articles that can be adjusted to achieve a more conforming fit to the wearer. Moreover, the inspection and removal of soiled absorbent articles that have integral side panels, such as conventional training pants, have not always been completely satisfactory. For example, the side panels have been difficult to tear when attempting to remove the article from the waist of the wearer instead of pulling the article down over the hips of the wearer.

Accordingly, despite the attempts to develop improved absorbent articles, there remains a need for absorbent articles that are adjustable to conform to the wearer for effective containment of bodily exudates, are capable of being pulled up and/or down over the hips and buttocks of the wearer, are readily secured about and removed from the wearer in a convenient and clean manner and are easily inspected by the caregiver to determine whether the article is soiled.

SUMMARY OF THE INVENTION

The present invention is directed to a pant-like, refastenable disposable absorbent article having side seams which include a front ear passively bonded to a back ear, wherein the front ear is releasable from the back ear preferably without tearing or damaging the back ear more than the front ear and, most preferably, without tearing or damaging the back ear or negatively affecting its tensile strength.

In accordance with one embodiment of this invention, the side seams include passive bonds for maintaining the diaper in the prefastened condition, particularly when it is being pulled over the hips of the wearer. The passive bonds can be easily broken or destroyed to release or disconnect the front waist region from the back waist region. In such a configuration, the passive bonds assist the fasteners in maintaining the diaper in a prefastened configuration as the diaper is pulled over the hips of the wearer. Moreover, the passive bonds prevent movement and shifting of the side edges of the front waist region and the back waist region relative to each other for improved ease of use, fit and performance. The passive bonds also provide improved hip coverage and prevent rollover or folding of the side edges and the waist edges of the prefastened diaper as the prefastened diaper is pulled over the wearer's hips. Such prevention of rollovers and folding can reduce the contact between the fasteners and the skin of the wearer, thus, resulting in reduced skin irritation and redness.

The passive bonds can be provided by any type of bonding well known to those skilled in the art, such as thermal, adhesive and ultrasonic bonding, and can be discrete point bonds, dashed lines, continuous lines, discontinuous lines and the like or combinations thereof. The passive bonds can have any suitable shape such as circular, square, triangular and the like. Further, the passive bond patterns can be designed having different pin diameters and various pin pattern configurations. The pin diameter and pin configuration provide a greater sheer strength in the cross-machine or lateral direction (CD) than a peel strength in the machine or longitudinal direction (MD), to maintain a pant-like form during use, and provide the passive bond which can be easily opened for use as a diaper rather than a pant.

In a particular embodiment of this invention, the side seam includes two dissimilar materials. For example, each side seam can include a first tearable material passively bonded to a second material, different from the first material.

The second material desirably has a basis weight greater than the basis weight of the first material. Desirably, the second material has a basis weight of at least about 20 gsm, more desirably at least about 30 gsm, while the first material has a basis weight less than the second material, desirably, less than about 30 gsm, more desirably less than about 20 gsm. For example, the first material can have a basis weight of less than about 20 gsm while the second material has a basis weight at least about 20 gsm, more desirably, the first material has a basis weight of less than about 20 gsm while the second material has a basis weight of at least about 30 gsm.

In one particular embodiment of this invention, the first material and the second material each has a basis weight of about 15 gsm to about 150 gsm, more desirably about 20 gsm to about 80 gsm, and still more desirably about 30 gsm to about 60 gsm, with the first material having a basis weight lower than the second material. Additionally, the second material desirably has a peak load grab tensile strength of about 8.5 lbs. to about 100 lbs., more desirably about 10.0 lbs. to about 60.0 lbs., measured using ASTM Procedure D 5034.

Bonding two dissimilar materials at the side seam, for example a front ear and a back ear, using passive bonds allows the front ear to tear more easily than the back ear. In accordance with one embodiment of the invention, the back ear or the portion of the back waist region including the tearable second material, tears desirably less than about 100% of the time, more desirably less than about 50% of the time and still more desirably never tears. In one embodiment, the front ear or the portion of the front waist region including the first material tears when the passive bonds are broken.

With the foregoing in mind, it is a feature and advantage of the invention to provide a pant-like, refastenable disposable absorbent article having side seams which include a front ear passively bonded to a back ear, wherein the front ear is releasable from the back ear without tearing or damaging the back ear more than the front ear and, most preferably, not damaging the back ear or negatively affecting its tensile strength.

It is further a feature and advantage of the invention to provide a pant-like, refastenable disposable absorbent article having side seams which include a front ear passively bonded to a back ear, wherein the front ear is made of a material having a basis weight less than a basis weight of the material forming the back ear.

Definitions

As used herein, the term "convertible" refers to an absorbent article that can be pulled on like a pant or applied as a diaper. The article can also be removed as either a pant or a diaper. The user has the option of application/removal that suits the situation.

As used herein, the term "disposable" refers to articles which are intended to be discarded after a limited use and that are not intended to be laundered or otherwise restored for reuse.

As used herein, the term "ear" refers to any material that extends laterally beyond the crotch area at the front or rear of the absorbent article.

As used herein, the terms "elastic," "elasticized" and "elasticity" refer to a property of a material or composite by virtue of which the material or composite tends to recover its original size and shape after removal of a force causing a deformation.

As used herein, the term "elastomeric" refers to a material or composite which can be elongated by at least 50 percent of its relaxed length in any direction and which will recover, upon release of the applied force, at least 40 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

As used herein, the term "extensible" refers to a material or composite which can be elongated by at least about 50 percent of its relaxed length in any direction and tends not to recover, or recovers less than 40 percent of its elongation, after removal of a force causing a deformation.

As used herein, the term "inelastic" refers to materials which are not elastomeric, either because they cannot be sufficiently stretched (by the above amount), or because they do not sufficiently retract (by the above amount) when stretched and relaxed.

As used herein, the terms "necked" and "neck stretched" are interchangeable terms that refer to a method of elongating an inelastic nonwoven fabric, generally in the longitudinal, or machine direction of the fabric, to reduce its width in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.4 times. The resulting neck-stretched fabric can be extended in the lateral (cross-machine) direction of the fabric during subsequent use, causing the fabric to return toward its original pre-necked configuration. Neck stretching processes are disclosed, for example, in U.S. Pat. No. 4,443,513 to Meitner et al.; U.S. Pat. Nos. 4,965,122, 4,981,747 and 5,114,781 to Morman; and U.S. Pat. No. 5,244,482 to Hassenboehler Jr. et al.

As used herein, the term "passive bond" refers to a bond which has a relatively low peel strength such that the bond can be easily broken by hand if desired to assist in inspecting or removing an absorbent article from the wearer, without tearing or severely damaging the other portions of the article, if desired, and without causing trauma to the wearer or spillage of waste materials from the absorbent article. Preferably, for example the passive bond can be broken without tearing or damaging the back ear more than the front ear and, most preferably, without tearing or damaging the back ear or negatively affecting its strength.

As used herein, the term "permanently bonded" refers to the joining, adhering, connecting, attaching, or the like, of two elements of an absorbent article such that the elements tend to be and remain bonded during normal use conditions of the absorbent article. Permanent bonds generally cannot be torn by hand without severely tearing or damaging the surrounding portions of the article.

As used herein, the term "prefastened" refers to a condition wherein the absorbent article has a fastening feature which is engaged or fastened prior to use by the wearer. For example, the fastening feature of the absorbent article may be engaged or fastened during the manufacturing process.

As used herein, the term "refastenable" refers to the property of two elements being capable of releasable attachment, separation, and subsequent releasable reattachment without substantial permanent deformation or other damage to either element.

As used herein, the term "releasably attached," "releasably engaged" and variations thereof refer to two elements being connected or connectable such that the elements tend to remain connected absent a separation force applied to one or both of the elements, and the elements being capable of separation without substantial permanent deformation or other damage. The required separation force is typically beyond that encountered while wearing the absorbent article.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

FIGS. 7-16 representatively show passive bonding patterns produced using various pin pattern configurations and different pin dimensions, according to one embodiment of this invention.

DETAILED DESCRIPTION OF THE INVENTION

Figure 1:
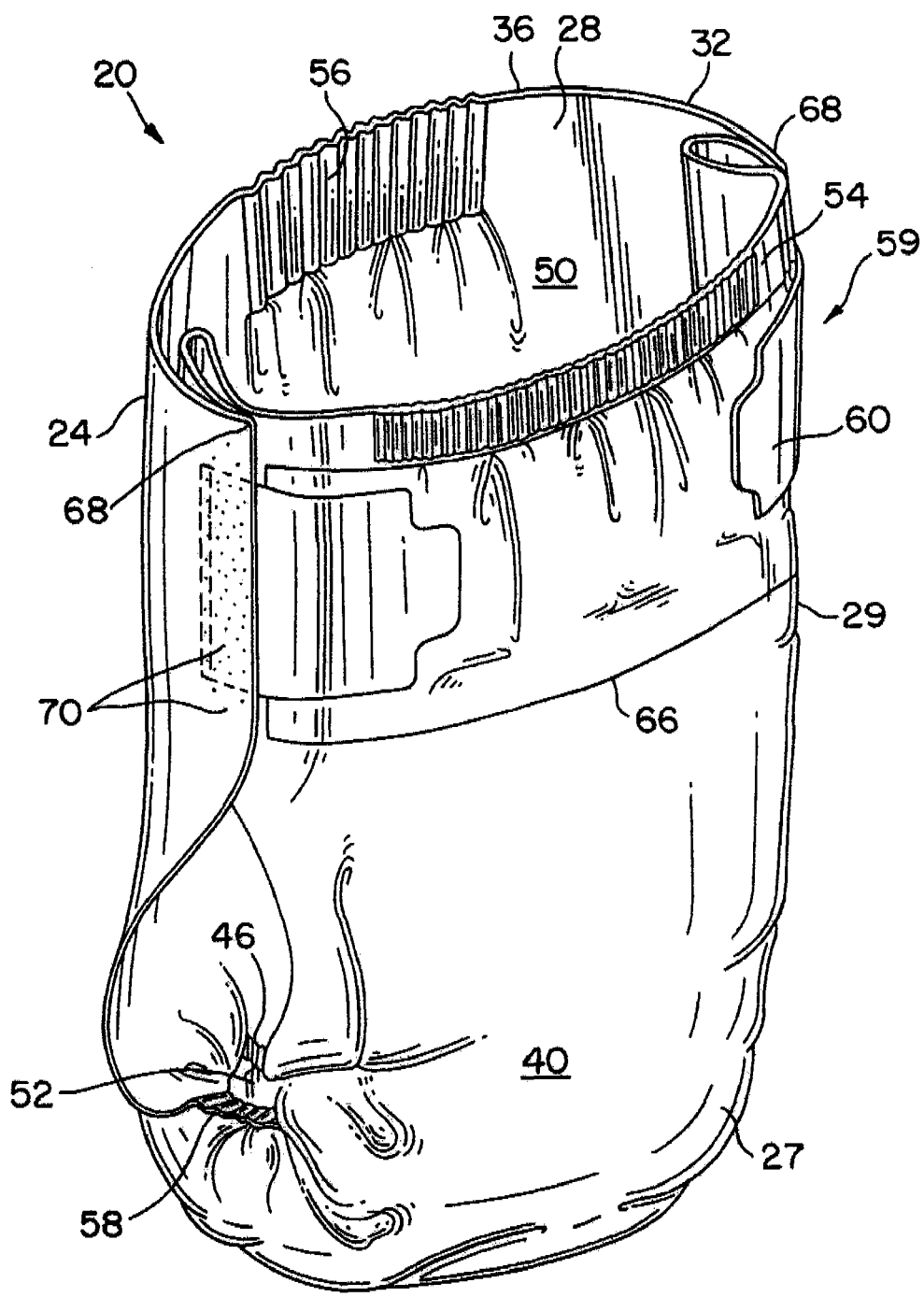
FIG. 1 representatively shows a perspective view of a pant-like prefastened, disposable absorbent article, according to one embodiment of this invention.

The present invention is directed to a refastenable, prefastened pant-like disposable absorbent article adaptable to be worn adjacent to the body of a wearer to absorb and contain various exudates discharged from the body. The absorbent article is initially fastened, or prefastened, so the absorbent article can be pulled over the wearer's hips and buttocks and positioned properly to effectively absorb and/or contain the body exudates. The prefastened absorbent article is also refastenable such that the absorbent article can be adjusted or fitted to the wearer's waist size and easily inspected to determine whether the absorbent article has been soiled. As such, the pant-like prefastened, disposable absorbent article of the present invention can function in a similar manner to conventional training pants when left in the prefastened configuration, or can be unfastened prior to or during use to function in a refastenable manner similar to a conventional diaper.

The pant-like disposable absorbent article of the present invention will be described in terms of a pant-like disposable diaper 20 that is adapted to be worn by infants about the lower torso. In particular, the pant-like disposable absorbent article will be described in terms of a refastenable, prefastened pant-like disposable diaper. It is apparent that the articles and methods of the present invention are equally adaptable for other types of absorbent articles such as adult incontinent products, training pants, feminine hygiene products, other personal care or health care garments, and the like.

Referring to FIGS. 1-6, a prefastened pant-like disposable diaper 20 of the present invention includes an absorbent chassis 27 and a fastening system 59. The absorbent chassis 27 defines a front waist region 22, a back waist region 24, a crotch region 26 interconnecting the front waist region 22 and the back waist region 24, an inner surface 28 which is configured to contact the wearer, and an outer surface 29 opposite the inner surface 28 which is configured to contact the wearer's clothing.

Figure 4:
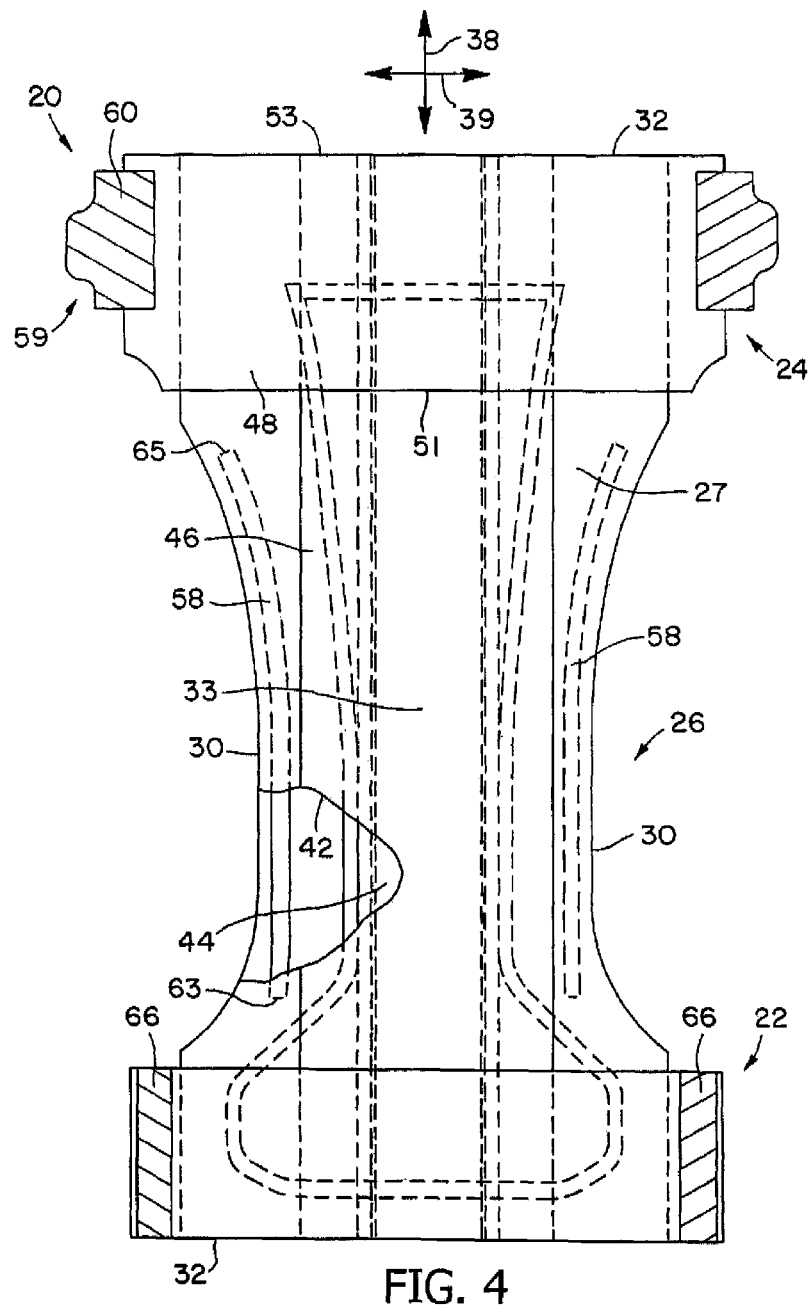
FIG. 4 representatively shows a plan view of the pant-like disposable absorbent article of FIG. 1 in an unfastened, stretched and laid flat condition with a surface of the article which contacts the wearer's skin facing the viewer, and with a portion of the article partially cut away to show the underlying features, according to one embodiment of this invention.

The illustrated absorbent chassis 27 includes a composite structure 33. The composite structure 33 includes an outer cover 40, a bodyside liner 42 which is connected to the outer cover 40 in a superposed relation, and an absorbent core 44 sandwiched between and, in certain embodiments, operatively joined to the outer cover 40 and/or the bodyside liner 42. The composite structure 33 may also include containment flaps 46, as shown in FIG. 4.

Figure 5:
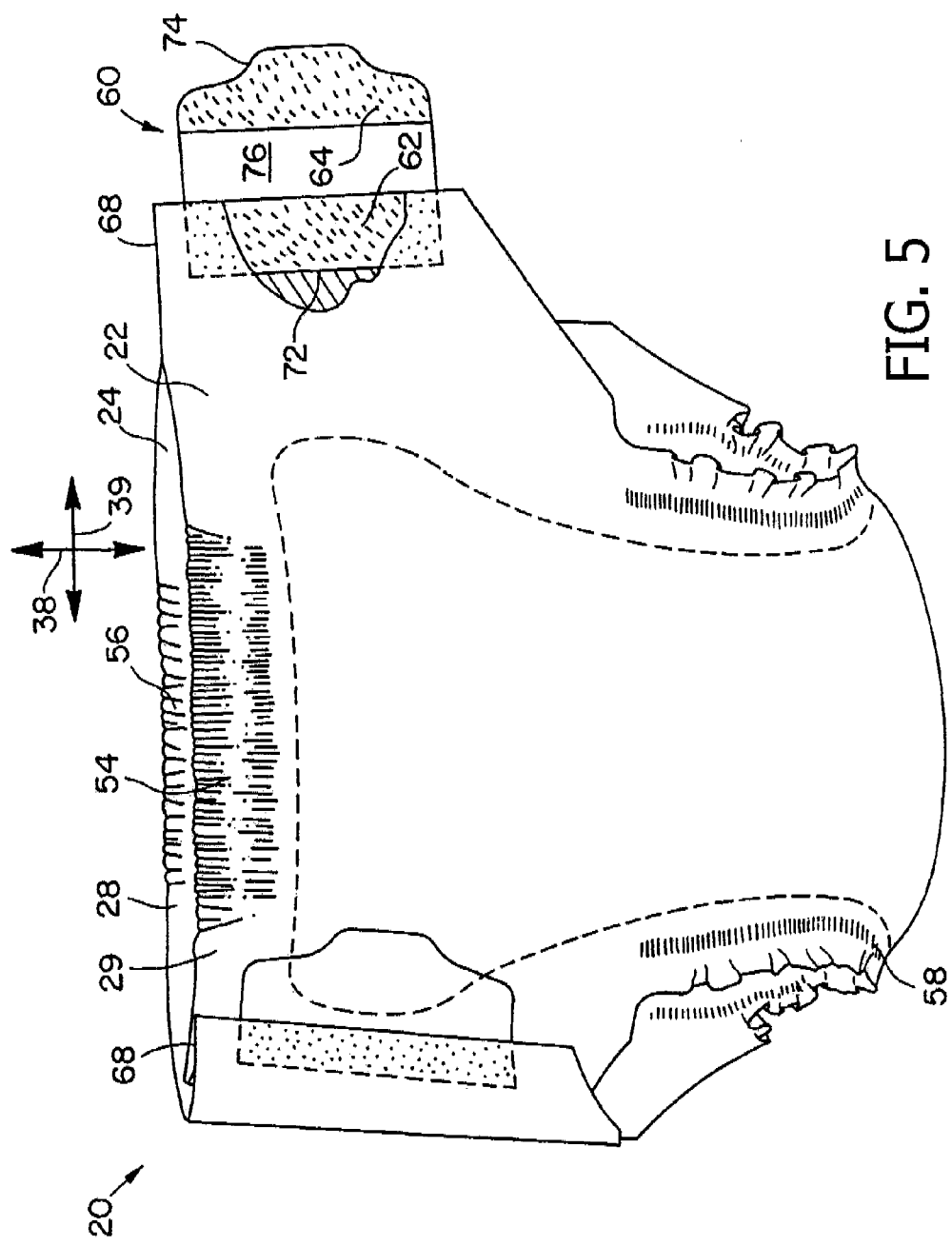
FIG. 5 representatively shows a front plan view of a pant-like prefastened, disposable absorbent article having a waist size adjustment means in an unengaged position, and with portions of the article partially cut away to show the underlying features, according to one embodiment of this invention.

The composite structure 33 further defines a pair of longitudinally opposite waist edges 32 that are generally defined by the waist edges of the absorbent chassis 27 and define a waist opening 50 that is configured to encircle the waist of the wearer when worn, and laterally opposed side edges 30 that are generally defined by the side edges of the absorbent chassis 27 and define leg openings 52 that may be curvilinear. For reference, arrows 38 and 39 depicting the orientation of the longitudinal axis and the lateral axis, respectively, of the diaper 20 are illustrated in FIGS. 3-5.

With the diaper 20 in the fastened position as illustrated in FIG. 1, the front waist region 22 and the back waist region 24 are joined together to define a three-dimensional pant configuration having the waist opening 50 and the leg openings 52. The front waist region 22 includes the portion of the diaper 20, which when worn, is positioned on the front of the wearer while the back waist region 24 includes the portion of the diaper 20 which, when worn, is positioned on the back of the wearer. The crotch region 26 of the diaper 20 includes the portion of the diaper 20 which, when worn, is positioned between the legs of the wearer and covers the lower torso of the wearer.

The absorbent chassis 27 is configured to contain and/or absorb any body exudates discharged from the wearer. For example, the absorbent chassis 27 desirably, although not necessarily, includes the pair of containment flaps 46 which are configured to provide a barrier to the transverse flow of body exudates. The containment flaps 46 may be located along the laterally opposed side edges 30 of the absorbent chassis 27. Each containment flap 46 typically defines an unattached edge that is configured to maintain an upright, perpendicular configuration in at least the crotch region 26 of the diaper 20 to form a seal against the wearer's body. Each containment flap 46 can be located along the transversely opposed side edges of the absorbent chassis 27, and can extend longitudinally along the entire length of the absorbent chassis 27 or may only extend partially along the length of the absorbent chassis 27. Suitable constructions and arrangements for the containment flaps 46 are generally well known to those skilled in the art and are described in U.S. Pat. No. 4,704,116 issued Nov. 3, 1987 to Enloe, the disclosure of which is incorporated herein by reference.

Figure 2:
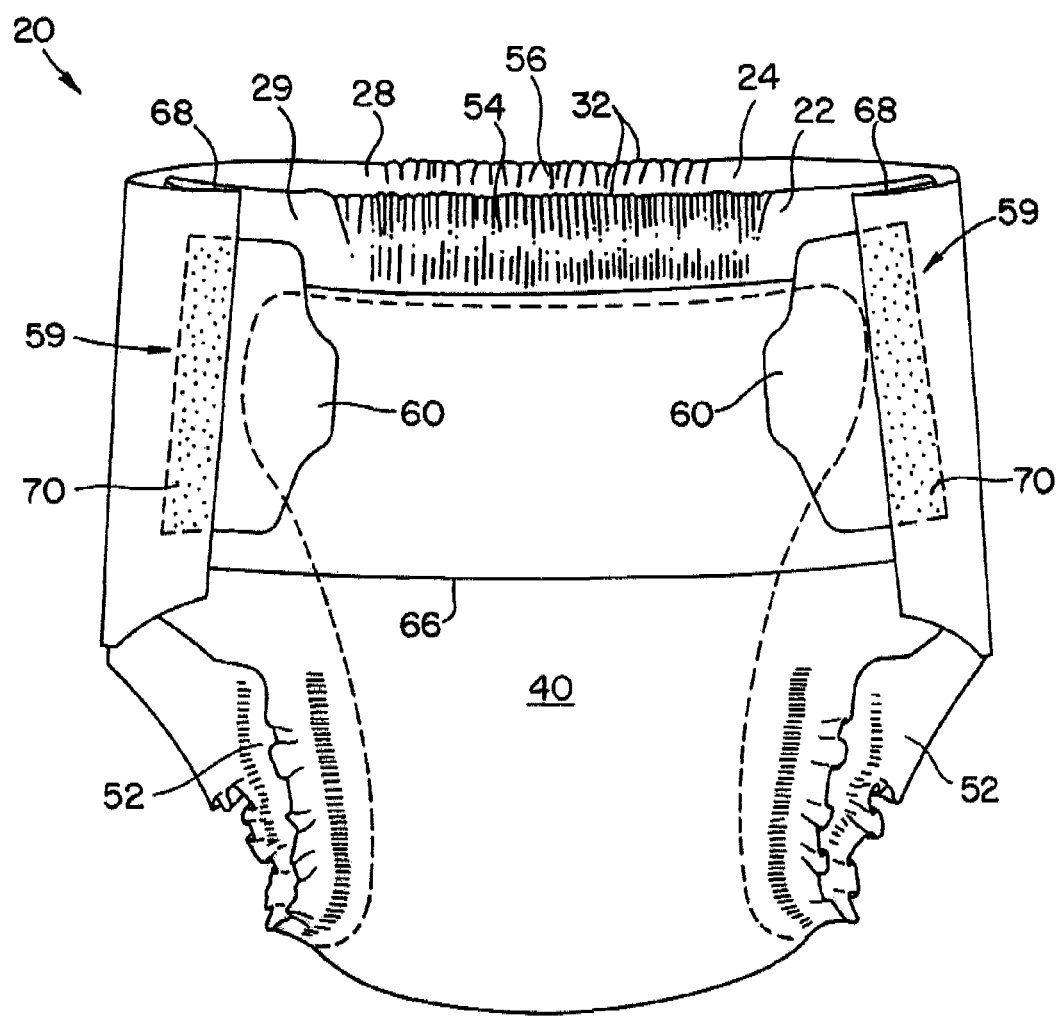
FIG. 2 representatively shows a front plan view of the pant-like prefastened, disposable absorbent article of FIG. 1, according to one embodiment of this invention.
Figure 3:
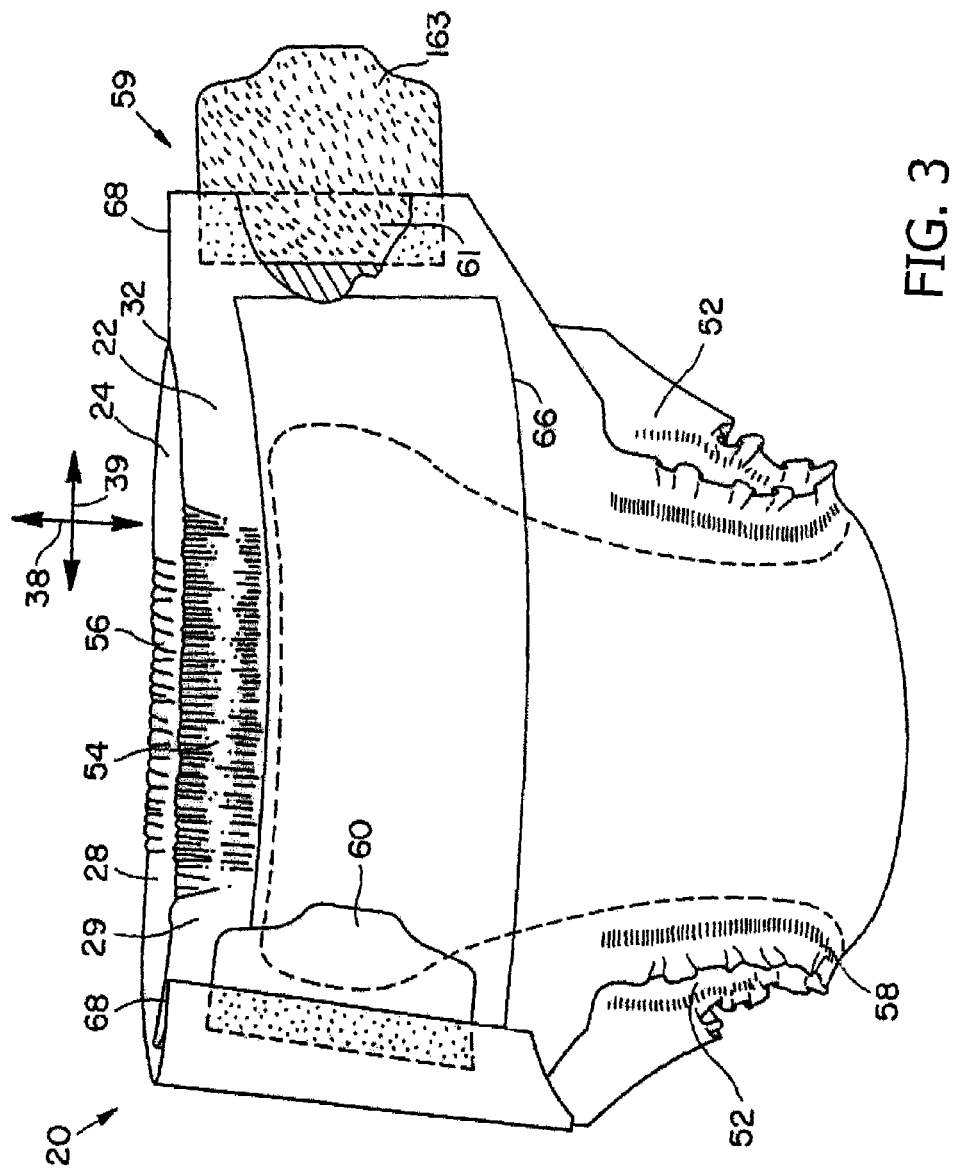
FIG. 3 representatively shows a front plan view of the pant-like prefastened, disposable absorbent article of FIG. 1 with a waist size adjustment means in an unengaged position, and with portions of the article partially cut away to show the underlying features, according to one embodiment of this invention.

To further enhance containment and/or absorption of body exudates, the diaper 20 desirably includes a front waist elastic member 54, a rear waist elastic member 56, and leg elastic members 58, as are known to those skilled in the art (FIGS. 1-3). The waist elastic members 54 and 56 can be operatively joined to the outer cover 40 or the bodyside liner 42 along the longitudinally opposed waist edges 32, and can extend over part or all of the waist edges.

The leg elastic members 58 are desirably operatively joined to the outer cover 40 and/or the bodyside liner 42 along the laterally opposed side edges 30 and positioned in the crotch region 26 of the diaper 20. The leg elastic members 58 are desirably longitudinally aligned along each side edge 30 of the composite structure 33. Each leg elastic member 58 has a front terminal point 63 and a back terminal point 65 which points represent the longitudinal ends of the elastic gathering caused by the leg elastic members.

Materials suitable for use as the waist elastic members 54 and 56 and the leg elastic members 58 are well known to those skilled in the art. For example, sheets, strands or ribbons of a polymeric, elastomeric material may be adhered to the outer cover 40 in a stretched position, or attached to the outer cover 40 while the outer cover 40 is pleated, such that elastic constrictive forces are imparted to the outer cover 40. The leg elastic members 58 may also include such materials as polyurethane, synthetic rubber and natural rubber.

In accordance with one embodiment of this invention as shown in FIG. 4, the diaper 20 includes a fit panel 48 superimposed adjacent to the waist edge 32 in at least one of the front waist region 22 and the back waist region 24, to provide a more comfortable, contouring fit about the wearer. Desirably, the fit panel 48 is elastic, elastomeric or extensible in at least one direction, such as the cross-machine or lateral direction. For example, as shown in FIG. 4, the diaper 20 includes the extensible fit panel 48 on the inner surface 28 of the diaper 20 that is configured to elongate in the lateral direction to provide an improved fit range and enhanced appearance of the diaper 20. Desirably, the extensible fit panel 48 allows the waist opening 50 to be adjusted, thereby increasing the waist perimeter dimension to assist in applying the diaper 20 onto the wearer. The fit panel 48 is also configured with respect to the diaper 20 such that the absorbent core 44 has the ability to move and receive body exudates without adversely affecting the positioning of the fit panel 48 and the diaper 20 about the waist of the wearer. Thus, movements of the wearer may cause the absorbent core 44 to move but do not adversely affect the overall positioning and fit of the diaper 20 on the wearer. Such improved fit can result in reduced leakage from the diaper 20, increased comfort and a more aesthetically pleasing appearance.

As shown in FIG. 4, in accordance with one embodiment of this invention, the fit panel 48 is located on the inner surface 28 and extends longitudinally beyond the side edges of the absorbent core 44 so that the fit panel 48 is generally coterminous with the waist edge 32 in the respective front waist region 22 and/or back waist region 24. When located on the inner surface 28 of the diaper 20, the fit panel 48 may define a free edge 51 that extends longitudinally inward towards the crotch region 26 of the diaper 20. In accordance with one embodiment of this invention, the free edge 51 is configured to remain at least partially unattached to the bodyside liner 42 to allow the absorbent core 44 to move, for example expand, to receive and contain body exudates. The unattached free edge 51 allows a pocket to form between the fit panel 48 and the bodyside liner 42 to contain body exudates. Further, the free edge 51, as well as a waist edge 53, of the fit panel 48 may be linear or curvilinear to better fit the wearer. Desirably, if the free edge 51 is curvilinear, the waist edge 53 is also curvilinear to improve the manufacturing process and reduce manufacturing waste.

Suitable materials for producing the fit panel 48 include, but are not limited to, stretch-bonded laminate (SBL) materials, neck-bonded laminate (NBL) materials, elastomeric films, elastomeric foam materials, and the like. For example, suitable meltblown elastomeric fibrous webs are described in U.S. Pat. No. 4,663,220, issued May 5, 1987 to T. Wisneski et al., the disclosure of which has previously been incorporated by reference. Examples of suitable composite fabrics comprising at least one layer of a nonwoven material secured to a fibrous elastic layer are described in European Patent Application No. EP 090 010 published on Apr. 8, 1987 with the inventors listed as J. Taylor et al., the disclosure of which has previously been incorporated by reference. Examples of suitable NBL materials are described in U.S. Pat. No. 5,226,992, issued Jul. 13, 1993 to Morman, the disclosure of which has previously been incorporated by reference.

In accordance with one embodiment of this invention, the fit panel 48 may be attached to the diaper 20 in any suitable manner that provides the desired elastic or extensible properties. For example, the fit panel 48 may be attached to the diaper 20 using adhesive, ultrasonic, and/or thermal bonding techniques, and the like.

The diaper 20 may be of various suitable shapes. For example, in the unfastened configuration as shown in FIG. 4, the diaper 20 may have an overall rectangular shape, T-shape, or an approximate hourglass shape. Other suitable shapes, which are not shown, include oval, circular and triangular shape. In the shown embodiment, the diaper 20 has a general I-shape in an unfastened configuration. Examples of suitable diaper configurations and suitable diaper components are described in U.S. Pat. No. 4,798,603, issued Jan. 17, 1989 to Meyer et al.; U.S. Pat. No. 5,176,668, issued Jan. 5, 1993 to Bernardin; U.S. Pat. No. 5,176,672, issued Jan. 5, 1993 to Bruemmer et al.; U.S. Pat. No. 5,192,606, issued Mar. 9, 1993 to Proxmire et al.; and U.S. Pat. No. 5,509,915, issued Apr. 23, 1996 to Hanson et al., the disclosures of which are herein incorporated by reference. The various components and configurations of the diaper 20 according to embodiments of this invention provide a desired fit range, as well as softness, body conformity, reduced skin irritation, reduced skin hydration, improved containment of body exudates and improved aesthetics.

The various components of the diaper 20 are integrally assembled together employing various types of suitable attachment means, such as adhesive, sonic and thermal bonds and combinations thereof. In the shown embodiment, for example, the outer cover 40 and bodyside liner 42 are assembled to each other with an adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other components of the diaper 20, such as the waist elastics 54 and 56 and the leg elastics 58, can be assembled into the diaper 20 by employing the above-identified attachment mechanisms. Desirably, the majority of the diaper components are assembled together using ultrasonic bonding techniques for reduced manufacturing cost and improved performance.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown), thermal bonding or other joining technology known to those having ordinary skill in the art. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials can also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter thick polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. The outer cover 40 can be extensible, for example as described in U.S. patent application Ser. No. 09/563,417 filed on May 3, 2000 by Roessler et al., the disclosure of which is hereby incorporated by reference to the extent it assists the present disclosure.

In accordance with one embodiment of this invention, the liquid permeable bodyside liner 42 is connected to the outer cover 40 and is illustrated as overlying the outer cover 40, and may but need not have the same dimensions as the outer cover 40. The bodyside liner 42 is desirably compliant, soft feeling, and nonirritating to the wearer's skin. Further, the bodyside liner 42 may be less hydrophilic than the absorbent core 44, to present a relatively dry surface to the wearer, and may be sufficiently porous to be liquid permeable, permitting liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner 42 can be composed of a meltblown or spunbond web of polyolefin fibers. The bodyside liner 42 can also be a bonded-carded web composed of natural and/or synthetic fibers. The bodyside liner 42 can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation TRITON X-102. Other suitable surfactants are commercially available from Uniqema Inc., a division of ICI of New Castle, Del., under the trade designation Ahcovel, and from Cognis Corporation of Ambler, Pa., produced in Cincinnati, Ohio, and sold under the trade designation Glucopon 220. The surfactant can be applied by any conventional means, such as spraying, printing, brush coating or the like. The surfactant can be applied to the entire bodyside liner 42 or can be selectively applied to particular sections of the bodyside liner 42, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from Chisso Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

In accordance with one embodiment of this invention, the bodyside liner 42 is desirably made of an elastic or an extensible material. For example, the bodyside liner 42 may be made from an extensible material as described in U.S. patent application Ser. No. 09/563,417 filed on May 3, 2000 by Roessler et al. Desirably, these materials are elastic or extensible in at least a cross-machine direction, parallel to the lateral axis depicted by arrow 39 in FIG. 4.

As shown in FIG. 4, the absorbent core 44 can be positioned between the outer cover 40 and the bodyside liner 42. The absorbent core 44 can be any structure which is generally compressible, conformable, non-irritating to the wearer's skin, and capable of absorbing and retaining liquids and certain body wastes. The absorbent core 44 can be manufactured in a wide variety of sizes and shapes, and from a wide variety of liquid absorbent materials commonly used in the art. For example, the absorbent core 44 can suitably include a matrix of hydrophilic fibers, such as a web of cellulosic fluff, mixed with particles of a high-absorbency material commonly known as superabsorbent material. In a particular embodiment, the absorbent core 44 includes a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent core 44 to better contain and absorb body exudates. The concentration of the superabsorbent particles may also vary through the thickness of the absorbent core 44. Alternatively, the absorbent core 44 may comprise a laminate of fibrous webs and superabsorbent material or other suitable means of maintaining a superabsorbent material in a localized area.

Suitable high-absorbency materials for the absorbent core 44 include, but are not limited to, natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of suitable synthetic, polymeric, high-absorbency materials include, but are not limited to, the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core 44 include, but are not limited to, natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and similar compounds. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. Generally, it is desired that the high absorbency material be in the form of discrete particles. However, the high absorbency material may also be in the form of fibers, flakes, rods, spheres, needles, or the like. Generally, the high absorbency material is present in the absorbent core 44 in an amount of about 5 weight percent to about 90 weight percent, based on a total weight of the absorbent core 44.

The absorbent core 44 may have any suitable shape. For example, the absorbent core 44 may be rectangular, I-shaped, or T-shaped. Desirably, the absorbent core 44 is narrow in the crotch region 26 of the diaper 20. The absorbent core 44 desirably has a width in the crotch region 26 of about 2.5 centimeters to about 12.7 centimeters (1.0 inch to about 5.0 inches), more desirably not greater than about 7.6 centimeters (3.0 inches) and still more desirably not greater than about 5.1 centimeters (2.0 inches). The narrow width of the absorbent core 44 in the crotch region 26 allows the absorbent core 44 to better fit between the legs of the wearer. It is apparent that the dimensions and the absorbent capacity of the absorbent core 44 should properly correspond to the size of the intended wearer and the liquid loading imparted by the intended use of the diaper 20.

In accordance with one embodiment of this invention, a substantially hydrophilic tissue wrapsheet (not shown) may be employed to help maintain the integrity of the airlaid fibrous structure of the absorbent core 44. The tissue wrapsheet is typically placed about the absorbent core 44 over at least the one major facing surface thereof and composed of an absorbent cellulosic material, such as creped wadding or a high wet-strength tissue. In accordance with one embodiment of the invention, the tissue wrapsheet can be configured to provide a wicking layer that helps to rapidly distribute liquid over the mass of absorbent fibers comprising the absorbent core 44. The tissue wrapsheet on one side of the absorbent fibrous mass may be bonded to the tissue wrapsheet located on the opposite side of the fibrous mass to effectively entrap the absorbent core 44. In accordance with one embodiment of this invention, the tissue wrapsheet may be necked, pleated and/or have any suitable design known to those having ordinary skill in the art to extend in at least one direction, for example the lateral or cross-machine direction, without tearing or ripping.

The diaper 20 according to the present invention also includes a fastening system 59 for securing the diaper 20 about the waist of the wearer. The fastening system 59 includes two laterally opposed fastening components or fasteners 60 located on one of the front waist region 22 and the back waist region 24 of the diaper 20 which are configured to releasably engage the opposite waist region to maintain the diaper 20 about the waist of the wearer. Fasteners 60 which are releasably engageable allow for ease of securing and removing the diaper 20 from the waist of the wearer without undesirably soiling the wearer. Further, refasteneable fasteners 60 readily allow for the inspection of the diaper 20 to determine if it has been soiled with the ability to refasten it if it is not soiled.

Desirably, each fastener 60 is permanently bonded, adhered or otherwise attached directly or indirectly to the diaper 20 at or laterally inward from the side edge 30, in one of the front waist region 22 or the back waist region 24. The fasteners 60 may be permanently bonded or attached in the vicinity of the side edges 30 of the diaper 20 by any means known to those skilled in the art, such as adhesive bonds, sonic bonds or thermal bonds.

In one embodiment of this invention, at least a portion of each fastener 60 can be releasably engagable directly with the outer surface 29 of the diaper 20 to provide improved fit and ease of fastening. Alternatively, as shown in FIGS. 1-3, the diaper 20 can include an attachment panel 66 located on the outer cover 40 in at least one of the front waist region 22 and the back waist region 24 of the diaper 20 to which each fastener 60 is refastenably engageable to maintain the diaper 20 about the waist of the wearer. The attachment panel 66 may include a single piece of material which extends substantially across the respective waist region of the diaper 20, as shown in FIGS. 1-3. Alternatively, the attachment panel 66 may include two separate panels located along the opposed side edges of the absorbent chassis 27 in one of the front waist region 22 and the back waist region 24, as shown in FIG. 4.

In accordance with one embodiment of this invention, the fasteners 60 are refastenably engaged with the attachment panel 66 positioned on the outer surface 29 of the front waist region 22 before the diaper 20 is placed on the wearer to provide a refastenable, prefastened pant-like disposable diaper 20. In such a configuration, the diaper 20 can be pulled on or off over the legs and hips of the wearer. If the pant-like diaper 20 becomes soiled during use, the fasteners 60 can be disengaged to easily remove the diaper 20 from the waist of the wearer with reduced risk of undesirably soiling the clothes or legs of the wearer. Thus, the diaper 20 is configured to be pulled on or off over the hips of the wearer such as conventional training pants and can be readily applied or removed by disengaging the fasteners 60, similar to conventional diaper articles. Moreover, the fasteners 60 can be repositioned after initial donning if necessary to adjust the fit of the diaper 20 to the wearer.

Alternatively, the fasteners 60 can be folded such that the fasteners 60 are releasably engaged with the attachment panel 66 or the outer surface 29 of the back waist region 24 before the diaper 20 is placed on the wearer. In such a configuration, the diaper 20 can be pulled on over the legs and hips of the wearer without the fasteners 60 engaging other components of the diaper 20 or any surrounding material which makes it difficult to apply the diaper 20. Further, the side seams 68 can be easily broken at the passive bonds 70, discussed below, if desired. After the initial donning of the diaper 20, the fasteners 60 can be disengaged from the back waist region 24 and engaged with the attachment panel 66 or the outer surface 29 of the front waist region 22 to adjust the waist perimeter dimension to properly fit the waist of the wearer.

As shown in FIG. 3, in accordance with one embodiment of this invention, the fasteners 60 may include a unitary, continuous fastening segment having a first engageable portion 61 that provides a prefastened, refastenable side seam 68 and a second engageable portion 163 that provides a waist size adjustment means. The use of fasteners 60 that provide both the side seam 68 and a waist size adjustment means with one continuous fastening segment advantageously simplifies the manufacturing process and reduces raw material requirements, resulting in reduced manufacturing costs.

When the first engageable portion 61 of each fastener 60 is refastenably engaged with the corresponding front waist region 22 and/or back waist region 24, providing the prefastened refastenable side seam 68, the laterally opposing side edges 30 of the diaper 20 each defines a leg opening 52 which is configured to encircle a leg of the wearer. Further, the waist edges 32 define the waist opening 50.

The second engageable portion 163 of each fastener 60 provides a waist size adjustment means, wherein the second engageable portion 163 is refastenably engageable directly with the outer surface 29 of the diaper 20 or alternatively with the attachment panel 66 which extends laterally across the outer surface 29 of the front waist region 22, as shown in FIGS. 1-3. The waist size adjustment means is configured to reduce the waist perimeter dimension of the waist opening 50 to further conform the waist opening 50 to the waist of the wearer after initial donning of the diaper 20 to provide improved fit.

Desirably, the first engageable portion 61 and the second engageable portion 163 are made of a suitable releasably engageable fastener, such as an adhesive tape tab fastener, hook fastener, loop fastener, mushroom fastener, snap, pin, belt and the like, and combinations thereof. For example, as shown in FIG. 3, the second engageable portion 163 may include a plurality of hook type fasteners and the attachment panel 66 and/or the outer cover 40 may be configured to function as a complimentary loop type fastener.

In accordance with one embodiment of this invention as shown in FIGS. 1-3, the attachment panel 66 may include a single piece of material, such as a loop component material, that extends substantially across the respective waist region of the diaper 20. In this configuration, the attachment panel 66 located on the outer cover 40 may further extend beyond the side edges 30 of the diaper 20 and include a folded over portion to which the first engageable portion 61 of continuous fastener 60 is refastenably engaged to provide the prefastened refastenable side seams 68. The attachment panel 66 may also include an elastic or stretchable material.

As shown in FIG. 4, in a particular embodiment of this invention, the diaper 20 can include two separate attachment panels 66 located along the opposing side edges 30 on the inner surface 28 in the front waist region 22. The first engageable portion 61 of each fastener 60, which is permanently bonded or attached to the diaper 20 at the back waist region 24, is releasably engageable with the corresponding attachment panel 66 to provide a releasable side seam 68. The second engageable portion 163 of each fastener 60 is releasably engaged to the respective attachment panels 66 to provide the waist size adjustment means. Alternatively, if the fasteners 60 are located on the front waist region 22, the attachment panels 66 may be located along the inner surface 28 of the diaper 20 in the back waist region 24. The attachment panels 66 may be otherwise located on the outer surface 29 of the diaper 20 at the front waist region 22 and/or the back waist region 24, depending upon the location of the fasteners 60. In such configurations, the prefastened, refastenable side seams 68 may be formed as described above, provided that the inner surface 28 or the outer surface 29 of the diaper 20 to which the attachment panels 66 are attached, are configured to be exposed to the first engageable portions 61 of the fastener 60.

Desirably, the side seams 68 are configured such that the outer surface 29 of the front waist region 22 is refastenably attached to the inner surface 28 of the back waist region 24. As such, multiple benefits are realized. For example, the longitudinally inward folded portion of the front waist region 22 ensures that none of the side seam 68 and the fastener 60 is exposed to the wearer's skin, reducing undesirable skin irritation. Moreover, in such a configuration, the fastener 60 is subjected to shear forces in use, such that the diaper 20 is more securely fastened upon the wearer. Finally, the fasteners 60, permanently bonded or attached to the back waist region 24 of the diaper 20, refastenably engage the diaper 20 in the front waist region 22 increasing the ease with which the wearer or the caregiver can adjust the fit of the diaper 20.

In a particular embodiment of this invention as shown in FIG. 5, each fastener 60 may include a primary fastener 62, and the waist size adjustment means, for example a secondary fastener 64. The primary fastener 62 may be permanently bonded or attached to the side edge 30 in one of the front waist region 22 and the back waist region 24 and refastenably attached to the side edge 30 in the opposite waist region 22 or 24 to provide the refastenable side seams 68.

The secondary fasteners 64 extend from the refastenable side seams 68 to form the waist size adjustment means. The secondary fasteners 64 are configured to encircle the hips of the wearer and engage the outer surface 29 of the front waist region 22 of the diaper 20 or alternatively, the attachment panel 66, to reduce the waist perimeter dimension of the waist opening 50 and conform the waist opening 50 to the wearer's waist. It is apparent that the secondary fasteners 64 may alternatively be located on the front waist region 22 and may be configured to releasably engage the outer surface 29 of the back waist region 24. Alternatively, the diaper 20 may include a single secondary fastener 64 extending from one of the refastenable side seams 68.

As shown in FIG. 5, the fasteners 60, when configured with multiple engaging portions, can include an intermediate portion 76 between the primary fastener 62 and the secondary 64 fastener. For example, the fasteners 60 can include hook-type fastening elements in the multiple engaging portions 62 and 64 and the intermediate portion 76 can be devoid of hook-type fastening elements. Desirably, the intermediate portion 76 is made of an elastic or extensible material. Thus, the intermediate portion 76 provides improved fit and comfort to the wearer by allowing the fastener 60 more flexibility and range in engaging the attachment panel 66 and/or the outer surface 29 of the diaper 20, either or both of which may include a loop fastening material. Suitable materials for the intermediate portion 76 include, but are not limited to, stretch-bonded laminate (SBL) materials, neck-bonded laminate (NBL) materials, elastomeric films, elastomeric foam materials, and the like, such as described above as being suitable for the fit panel 48.

In accordance with one embodiment of this invention, the prefastened, refastenable side seams 68 on the diaper 20 may further include passive bonds 70 (which, themselves, are not refastenable) for maintaining the diaper 20 in the prefastened condition, particularly when it is being pulled over the hips of the wearer. Desirably, but not necessarily, the passive bonds 70 are easily broken or destroyed to release or disconnect the front waist region 22 from the back waist region 24. Absorbent articles including such passive bonds 70 and methods of making the passive bonds 70 are further described in U.S. patent application entitled "DISPOSABLE ABSORBENT ARTICLES HAVING PASSIVE SIDE BONDS AND ADJUSTABLE FASTENING SYSTEMS" filed in the name of Elsberg on Jun. 19, 1998 and assigned U.S. Ser. No. 09/100,574, and U.S. patent application entitled "METHOD OF MAKING AN ABSORBENT ARTICLE WITH PRE-FASTENED SIDE PANELS AND ABSORBENT ARTICLES MADE BY THE SAME" filed in the name of McNichols on Jun. 19, 1998 and assigned U.S. Ser. No. 09/100,825, the disclosures of which are hereby incorporated by reference.

Figure 6:
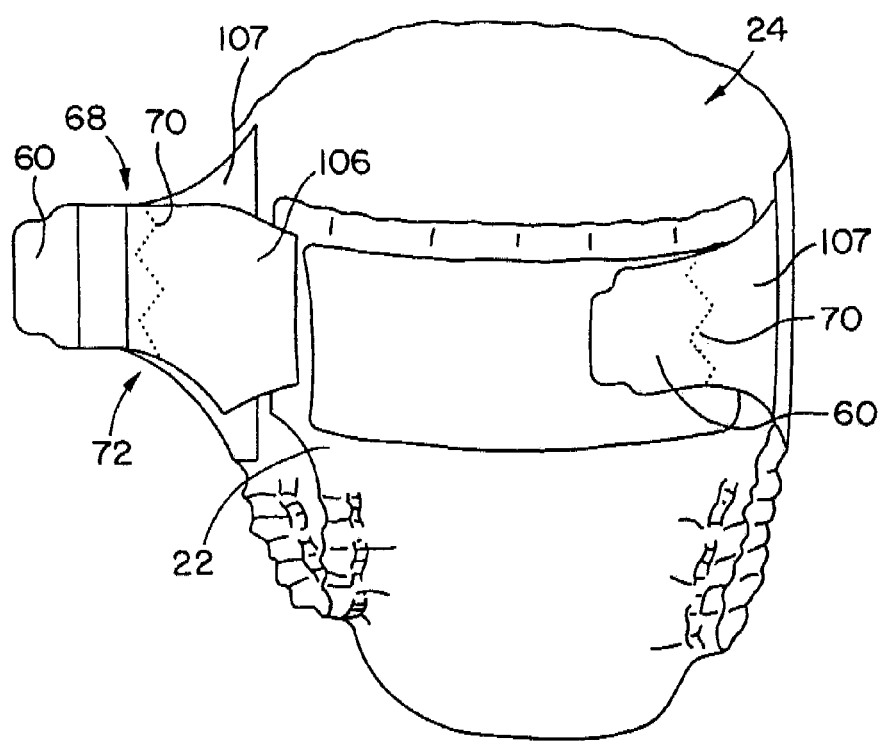
FIG. 6 representatively shows a front plan view of a pant-like prefastened, disposable absorbent article having a plurality of passive bonds forming a "zig-zag" bond pattern, according to one embodiment of this invention.
Figure 7:
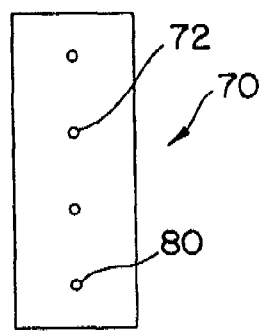
Figure 8:
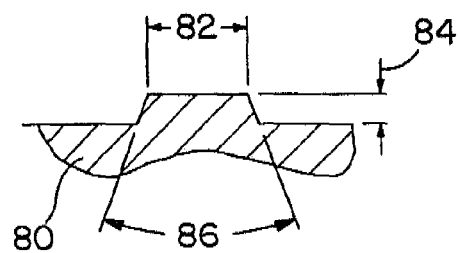
Figure 9:
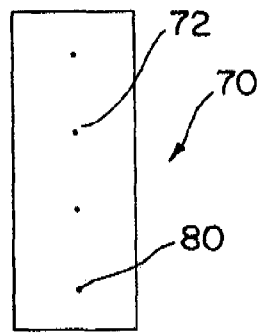
Figure 10:
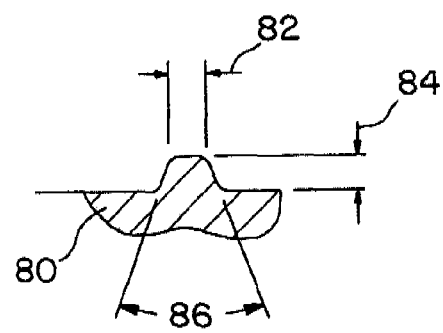

For example, as shown in FIGS. 1 and 6, the side seams 68 of the diaper 20 may include passive bonds 70 that releasably connect the side portion of the back waist region 24 to the corresponding side portion of the front waist region 22 of the diaper 20. In such a configuration, the passive bonds 70 may assist the first engageable portion 61 of the fasteners 60, that provide the refastenable side seams 68, in maintaining the diaper 20 in a prefastened configuration as the diaper 20 is pulled over the hips of the wearer. Moreover, the passive bonds 70 assist in securing the refastenable side seams 68 to prevent movement and shifting of the side edges 30 of the front waist region 22 and the back waist region 24 relative to each other for improved fit and performance. The passive bonds 70 also provide improved hip coverage and prevent rollover or folding of the side edges 30 and the waist edges 32 of the prefastened diaper 20 as the prefastened diaper 20 is pulled over the wearer's hips. Such prevention of rollovers and folding can reduce the contact between the fasteners 60 and the skin of the wearer, thus, resulting in reduced skin irritation and redness.

The passive bonds 70 may be located on the diaper 20 in any manner that provides the desired improved fastening while maintaining the desired elastic or extensible properties of the diaper components being bonded. For example, as shown in FIGS. 1 and 2, the passive bonds 70 may be located laterally inward of the side edges 30 of the front waist region 22 and/or the back waist region 24, adjacent to or included with the refastenable side seams 68. In such a configuration, the passive bonds 70 connect the front waist region 22 to the back waist region 24 of the diaper 20 in a facing relationship.

The passive bonds 70 can be provided by any type of bonding well known to those skilled in the art, such as thermal, adhesive and ultrasonic bonding, and can be discrete point bonds, dashed lines, continuous lines, discontinuous lines and the like or combinations thereof. The passive bonds 70 can have any suitable shape such as circular, square, triangular and the like. Desirably, the passive bonds 70 are ultrasonic point bonds, which can be destroyed upon the first opening of the diaper 20.

Figure 11:
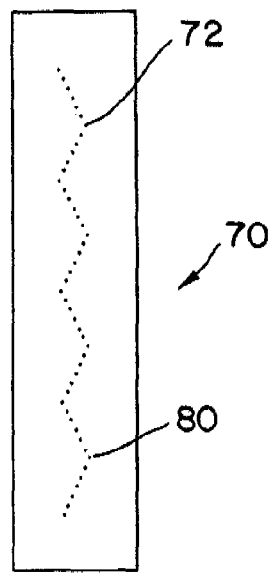

In accordance with one embodiment of this invention, the passive bond patterns 72 prevent a "zippering effect" whereby the passive bonds 70 are destroyed during use and affect the fit of the diaper 20 about the wearer. Thus, the bond patterns 72 can be designed having different pin diameters and various pin pattern configurations. The pin diameter and pin configuration provide a greater sheer strength in the cross-machine or lateral direction (CD) than a peel strength in the machine or longitudinal direction (MD), to maintain a pant-like form during use, and provide the passive bond 70 which can be easily opened for use as a diaper rather than a pant. Additionally, the bond configuration, for example a "zig-zag" pattern as shown in FIG. 11, may also increase the fit range, breaking at the individual end point bond first, but maintain overall bond pattern integrity during application and wear. An extended zig-zag pattern configuration allows the material to elongate around the wearer's waist and the passive bond 70 to expand without the bond opening or "zippering" under stress of wear.

For example, as shown in FIGS. 7-16, the passive bonds 70 can be ultrasonic point bonds which form various bond patterns 72 having a plurality of point bonds 80 with a surface diameter 82 and a height 84. Desirably, each point bond 80 has a surface diameter 82 of about 0.010 inch to about 0.125, more desirably about 0.030 inch to about 0.118 inches. The height 84 of the bond pins above the anvil is about 0.015 inch to about 0.070 inch, more desirably about 0.030 inch to about 0.040 inch, still more desirably about 0.035 inch. Desirably, but not necessarily, each point bond 80 forms a wall which extends from a surface of the point bond 80 to a surface of the diaper 20 to form an inclusive angle 86 of about 30° to about 80°, more desirably about 60°, as shown for example in FIG. 8.

As shown in FIGS. 7-10, the passive bonds 70 can have a bond pattern 72 forming a generally straight line wherein each point bond 80 has a surface diameter 82 of about 0.010 inch to about 0.125 inch and a pin height 84 of about 0.015 inch to about 0.070 inch. The passive bonds 70 can have a zig-zag bond pattern 72, as shown in FIG. 11, having a plurality of point bonds 80 each with a surface diameter 82 of about 0.030 inch to about 0.040 inch and a height 84 of about 0.030 inch to about 0.040 inch, as shown in FIG. 12.

Alternatively, the passive bonds 70 can form a generally arcuate or curved bond pattern 72 wherein a plurality of point bonds 80, for example three point bonds 80, are grouped together in a series, as shown in FIGS. 13 and 14. Each point bond 80 can have a surface diameter 82 of about 0.025 inch to about 0.035 inch and a height 84 of about 0.030 inch to about 0.040 inch. Further, as shown in FIGS. 15 and 16 the passive bonds 70 can form a sine-wave bond pattern 72 wherein each point bond 80 has a surface diameter 82 of about 0.035 inch to about 0.045 inch and a height 84 of about 0.030 inch to about 0.040 inch.

Figure 12:
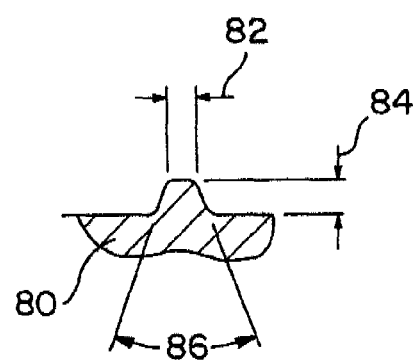

In a particular embodiment of this invention as shown for example in FIGS. 6 and 12, the passive bonds 70 having a zig-zag bond pattern 72 allow lateral side panels or ears 106 and 107 to elongate around a wearer's waist and to allow the side seam 68 to expand without the bonds opening or zippering from the stress of wear. Desirably, each side panel or ear 106 and 107 is elastic or extensible in at least one direction, for example the cross-machine direction. The zig-zag bond pattern 72 has greater strength in the cross-machine direction (shear) than in the machine direction (peel) in order to provide an easy opening joint, if desired, so that the diaper 20 can be opened along the side seams 68 for application or removal as a conventional diaper article.

As described above, the side seams 68 can be configured to be readily broken such that the caregiver can easily disengage the front waist region 22 and the back waist region 24 to inspect the diaper for soiling or to initially position the diaper 20 on the wearer if desired, and to remove the diaper 20 from the wearer after it has been soiled. Thus, it is desirable that the side seams 68 define a relatively low peel strength such that the caregiver can readily disengage the side seams 68 and break the passive bonds 70 to separate the front waist region 22 and the back waist region 24 to remove the diaper 20 from the waist of the wearer similar to conventional diapers that are not prefastened. Similarly, the caregiver or the wearer can easily disengage the waist size adjustment means from the outer surface 29 of the diaper 20 or the attachment panel 66. Thus, it is desirable that the waist size adjustment means define a relatively low peel strength. Suitable peel strength values for the waist size adjustment means are well known to those skilled in the art. One test for measuring peel strength of hook and loop fasteners is ASTM D1876-72. This test is described in U.S. Pat. No. 5,176,671, issued to Roessler et al., the disclosure of which is incorporated herein by reference.

In accordance with one embodiment of this invention, the absorbent article is convertible from a pant-like absorbent article, wherein the passive bonds 70 connect the front waist region 22 to the back waist region 24, to diaper-like absorbent article, wherein the passive bonds 70 are broken or torn to disengage the front waist region 22 from the back waist region 24. The diaper 20 can be easily opened by the flick of the caregiver's wrist or snapping of the diaper 20 in the caregiver's hand, wherein the passive bonds 70 are broken and the side seam 68 opens to disengage the front waist region 22 from the back waist region 24. In such a configuration, the diaper is applied as a conventional diaper article. This convertible feature allows the caregiver the choice as to how to apply the diaper 20.

In such a configuration, the diaper 20 has laterally opposing side panels or ears 106 connected to the front waist region 22 and laterally opposing side panels or ears 107 connected to the back waist region 24. Desirably, but not necessarily, the ears 106 and 107 are elastic or extensible. Fasteners 60 are permanently attached to either the front ears 106 or the back ears 107, as discussed above. For example, a fastener 60 is bonded to each back ear 107 at a distal end thereof. During manufacturing of the diaper 20, the fastener 60 is folded onto the elastic ear 107 so that the hook type fasteners attach to the elastic ear 107 and the diaper 20 is folded so that the front waist region 22 and the back waist region 24 are aligned with each other. Passive bonds 70 connect the front waist region 22 to the back waist region to form side seams 68. If the caregiver chooses, he or she may hold the diaper 20 and flick his or her wrist or snap the diaper 20 to break the passive bonds 70 connecting the front waist region 22 and the back waist region 24. The waist regions 22 and 24 disengage and the diaper 20 can be applied as a conventional diaper article.

Desirably, the passive bonds 70 have a peel strength of less than about 5000 grams, more desirably less than about 3000 grams, still more desirably less than about 2000 grams, measured in the machine direction (MD) of the article. Further, the passive bonds 70 desirably have a minimum machine direction (MD) peel strength of at least about 100 grams to about 600 grams, more desirably at least about 200 grams to about 400 grams. To measure the peel strength of the passive bonds 70, the diaper 20 was assembled, using only the passive bonds 70 to form the pant-like configuration of the diaper 20. The back waist region, including the back waistband, was placed in an upper jaw of a peel strength measuring instrument and the front waist region, including the front waistband, was placed in the lower jaw. The upper jaw and the lower jaw each are about one inch square having a 1 inch by 1.5 inch back plate attached thereto. Result of one peel strength test is shown in Table below.

In a particular embodiment of this invention, side seam 68 includes two dissimilar materials. For example, each side seam 68 can include a first tearable material passively bonded to a second material, different from the first material. A portion of the front waist region 22 (as shown in FIG. 5), the lateral side panel or front ear 106 (as shown in FIG. 6), or a portion of the attachment panel 66 positioned on the front waist region 22, for example, can comprise the first material, such as a point bonded nonwoven material. A portion of the back waist portion 24 (as shown in FIG. 5) or the lateral side panel or back ear 107 (as shown in FIG. 6), for example, can comprise the second material which is different from the first material, such as a KRATON-based film sandwiched between two layers of polypropylene spunbond (KNBL). Desirably, but not necessarily, the second material is elastic or extensible.

As shown in FIG. 6, the back ear 107 including the second material desirably has a basis weight greater than the basis weight of the front ear 106 including the first material. Desirably, the second material has a basis weight of at least about 20 gsm, more desirably at least about 30 gsm, while the first material has a basis weight less than the second material, desirably, less than about 30 gsm, more desirably less than about 20 gsm. For example, the first material can have a basis weight of less than about 20 gsm while the second material has a basis weight at least about 20 gsm, more desirably, the first material has a basis weight of less than about 20 gsm while the second material has a basis weight of at least about 30 gsm. In one particular embodiment of this invention, the first material and the second material each has a basis weight of about 15 gsm to about 150 gsm, more desirably about 20 gsm to about 80 gsm, and still more desirably about 30 gsm to about 60 gsm, with the first material having a basis weight lower than the second material. Additionally, the second material desirably has a peak load grab tensile strength of about 8.5 lbs. to about 100 lbs., more desirably about 10 lbs. to about 60 lbs., measured using ASTM Procedure STM-D 5034.

Bonding two dissimilar materials at the side seam 68, for example the front ear 106 and the back ear 107, using passive bonds 70 allows the front ear 106 to tear more easily than the back ear 107. The front ear 106 and the back ear 107 can be passively bonded using bonding means well known in the art. Desirably, the passive bonds 70 are ultrasonic point bonds. However, other bonding means known to those skilled in the art may be used. Desirably, the back ear 107 is sufficiently strong to support the application of the diaper 20 without tearing.

In accordance with one embodiment of the invention, the back ear or the portion of the back waist region including the tearable second material, tears desirably less than about 100% of the time, more desirably less than about 50% of the time and still more desirably never tears. In one embodiment, the front ear or the portion of the front waist region including the first material tears when the passive bonds are broken. As used herein, the term "tearing" refers to the breaking of at least some of the filaments or tearing some of the first material comprising the front ear 106 or the front waist region 22, for example, when the passive bond 70 is opened or broken by the caregiver or the wearer.

EXAMPLES

Example 1

The peel strength of the passive bonds, which at least partially form the pant-like configuration of the diaper, was tested to determine the amount of force required to break the passive bonds. For example, a caregiver may hold the diaper in his or her hand and flick his or her wrist to break the passive bonds of the diaper, if he or she desires to apply the diaper as a diaper-like article rather than a pant-like article.

The article was placed in a peel strength measuring instrument such that the back waist region, including the back waistband, was placed in an upper jaw of the peel strength measuring instrument and the front waist region, including the front waistband, was placed in the lower jaw. The upper-jaw and the lower jaw each are about one inch square having a 1 inch by 1.5 inch back plate attached thereto.

Five samples were tested having various passive bond patterns. Samples 1-4 were the most difficult of the samples to open and required a strong snap to break the passive bond patterns and open the article. The passive bonds of Sample 5 were easier to break than the passive bonds of Samples 1-4 and could be opened with a firm snap. Sample 6 could be opened with a light snap. Table 1 below shows the test results.

TABLE 1

Peel Strength and Ease of Opening

| Sample | Peak Load (grams) |
|---|---|
| 1 | 4202.7 |
| 2 | 4480.4 |
| 3 | 4428.4 |
| 4 | 4643.7 |
| 5 | 2849.8 |
| 6 | 1818.6 |

Example 2

Several samples were constructed having a first material bonded to a second material from the first material using ultrasonic passive bonds and then tested to determine which of the two materials will tear or be damaged as a result of breaking the passive bonds. Materials tested included the following code materials.

Code 1 was a liner made from a 0.5 osy polypropylene spunbond material necked about 35% and having a basis weight of about 17 gsm.

Code 2 was a film having a basis weight of about 19 gsm. The film is a vapor permeable film layer purchased from Huntsman Packaging under the experimental number XP 1985B. The film layer included 50% to 60% weight percent calcium carbonate with the remainder being liner low density polyethylene copolymer of ethylene-octene. The film is printed with blue graphics.

Code 3 was an outer cover made from a point bonded thermal laminate of the Code 2 film and a 0.4 osy polypropylene spunbond material necked about 35%. Code 3 had a basis weight of about 29 gsm.

Code 4 was a 1.5 osy point unbonded (PUB) side by side, polypropylene/polyethylene web of spunbond filaments having a basis weight of about 51 gsm.

Code 5 was a 2.0 osy point unbonded (PUB) side by side, polypropylene/polyethylene web of spunbond filaments having a basis weight of about 60 gsm.

Code 6 was a neck-bonded laminate (NBL) ear material including two necked polypropylene spunbond webs bonded to an elastomeric film between them, having a basis weight of about 132 gsm.

The strength of each material was tested using the standard testing procedure ASTM D 5034. Five samples of each material were tested in the machine direction of the manufactured material. The test results are displayed in Table 2, below. The Peak Load (Tensile Strength) is the average maximum load (gram force) before the specimen ruptures. The Peak Energy is the average area under the load-elongation curve from the origin to the point of rupture.

The first material was bonded to the second material using passive bonds. The passive bonds were then broken to determine which of the first material and the second material tore or was damaged as the passive bonds were broken. The test results displayed in Table 3, below.

TABLE 2

Strength of Material

| Material Code | Peak Load (lb.) | Energy (in.-lb.) |
|---|---|---|
| 1 | 8.4 | 3.72 |
| 2 | 3.8 | 3.16 |
| 3 | 10.4 | 6.9 |
| 4 | 17.8 | 17.47 |
| 5 | 19.8 | 15.58 |
| 6 | 51.5 | 23.73 |

Standard Test Procedure 149W

Test specimens about 4 inches wide and about 6 inches long were prepared. The test specimen was placed symmetrically in the clamps of a tensile tester equipped with an appropriate load cell and integrator or equivalent equipment, with the longer dimension parallel to the direction of the load application and the jaws were closed. The test specimen was stretched until rupture and values recorded.

TABLE 3

Tearing of Dissimilar Materials

| Set | Sample Codes | Material Facing Horn | Results | Tore, Shredded, Holes | Level of Damage to Material |
|---|---|---|---|---|---|
| 2A | Code 2/Code 1 | Code 2 | Code 2 shredded/Code 2 left on Code 1 | Code 2 | 3 |

TABLE 3-continued

Tearing of Dissimilar Materials

| Set | Sample Codes | Material Facing Horn | Results | Tore, Shredded, Holes | Level of Damage to Material |
|---|---|---|---|---|---|
| 2B | Code 1/Code 2 | Code 1 | Code 2 shredded/Code 2 left Code 1 | Code 2 | 3 |
| 2C | Code 3/Code 4 | Code 3 | Code 3 shredded, tore/Code 3 on Code 4 | Code 3 | 10 |
| 2D | Code 4/Code 3 | Code 4 | Code 3 shredded, tore/ Code 3 on Code 4 | Code 3 | 10 |
| 2E | Code 5/Code 6 | Code 5 | holes | Code 5 | 1 |
| 2F | Code 6/Code 5 | Code 6 | holes in both | Codes 5 and 6 | 2 |
| 2G | Code 1/Code 4 | Code 1 | holes, tears | Code 1 | 3 |
| 2H | Code 4/Code 1 | Code 4 | holes | Code 1 | 1 |
| 3A | Code 2/Code 4 | Code 2 | holes, shredded | Code 2 | 9 |
| 3B | Code 4/Code 2 | Code 4 | holes, shredded | Code 2 | 10 |
| 3C | Code 3/Code 5 | Code 3 | holes, shredded | Code 3 | 10 |
| 3D | Code 5/Code 3 | Code 5 | holes, shredded | Code 3 | 10 |
| 3E | Code 6/Code 1 | Code 6 | holes, tears | Code 1 | 5 |
| 3F | Code 1/Code 6 | Code 1 | holes, tears | Code 1 | 5 |
| 3G | Code 1/Code 5 | Code 1 | holes, tears | Code 1 | 6 |
| 3H | Code 5/Code 1 | Code 5 | holes, tears | Code 1 | 1 |
| 4A | Code 2/Code 5 | Code 2 | holes, shredded, Code 2 on Code 5 | Code 2 | 10 |
| 4B | Code 5/Code 2 | Code 5 | shredded, holes, Code 2 on Code 5 | Code 2 | 10 |
| 4C | Code 3/Code 1 | Code 3 | holes in both | Codes 1, 3 | 2 |
| 4D | Code 1/Code 3 | Code 1 | holes in both, shredded on Code 3 only | Codes 1, 3 | 7 |
| 4E | Code 6/Code 4 | Code 6 | holes in both | Codes 4, 6 | 2 |
| 4F | Code 4/Code 6 | Code 4 | holes in both | Codes 4, 6 | 2 |

* Level of Damage to Material is visually assessed on a scale of 1 (little damage) to 10 (severe damage).

FIGS. 17-27 show the first material (right) and the second material (left) after the passive bonds, which bonded the two materials together, were broken.

Figure 17:
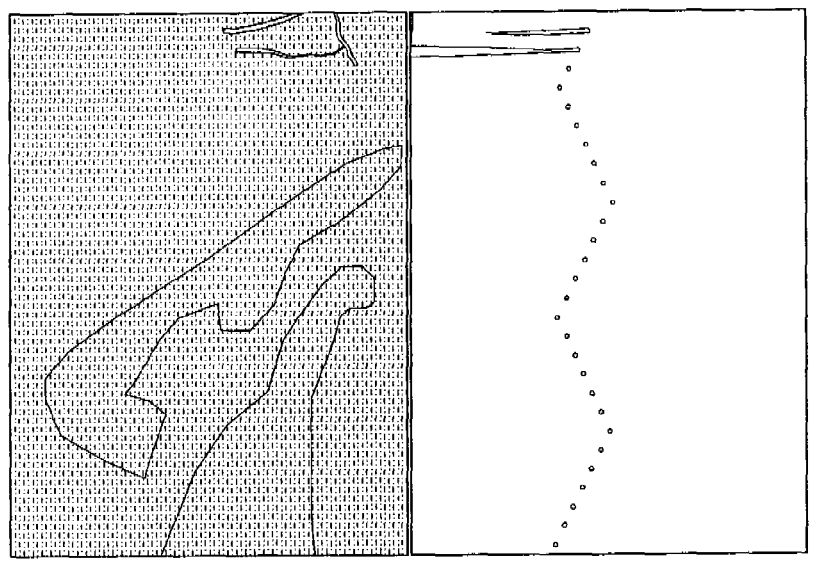
FIGS. 17-27 are photograpghs showing a first material and a second material after a passive bond bonding the two materials together has been broken, according to one embodiment of this invention.

FIG. 17 shows Code 1 (left) and Code 2 (right) after the passive bonds bonding the two materials together were broken. As shown in FIG. 17, Code 2 tore while Code 1 did not.

Figure 18:
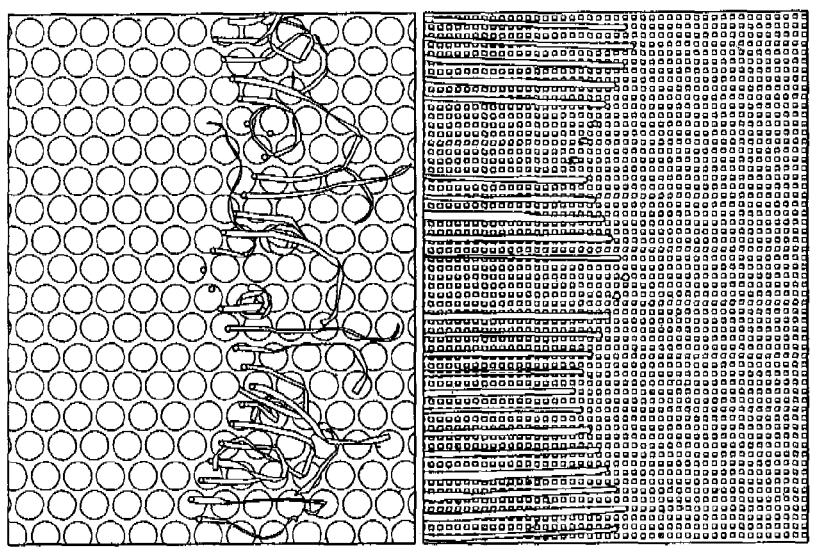

FIG. 18 shows Code 4 (left) and Code 3 (right) after the passive bonds bonding the two materials together were broken. As shown in FIG. 18, Code 3 tore while Code 4 did not.

Figure 19:
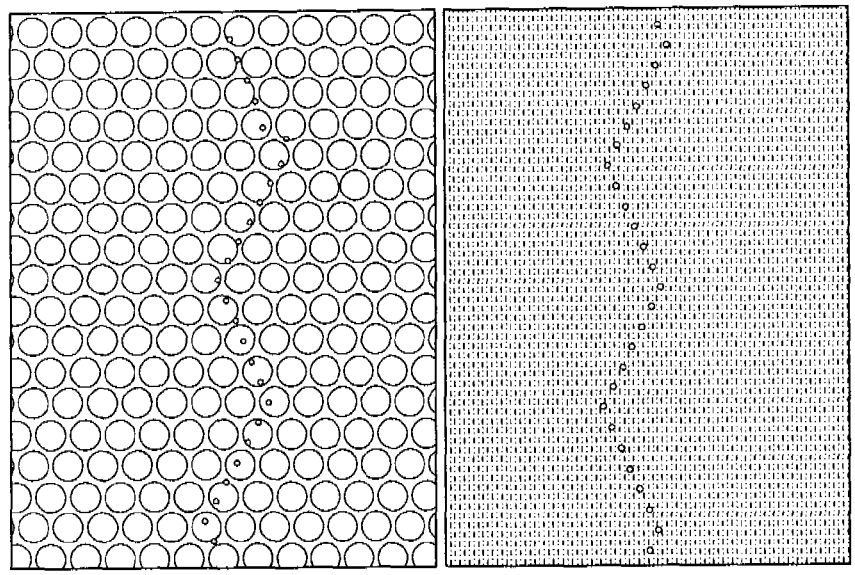

FIG. 19 shows Code 6 (left) and Code 5 (right) after the passive bonds bonding the two materials together were broken. As shown in FIG. 19, Code 5 and Code 6 contain holes resulting from breaking the passive bonds.

Figure 20:
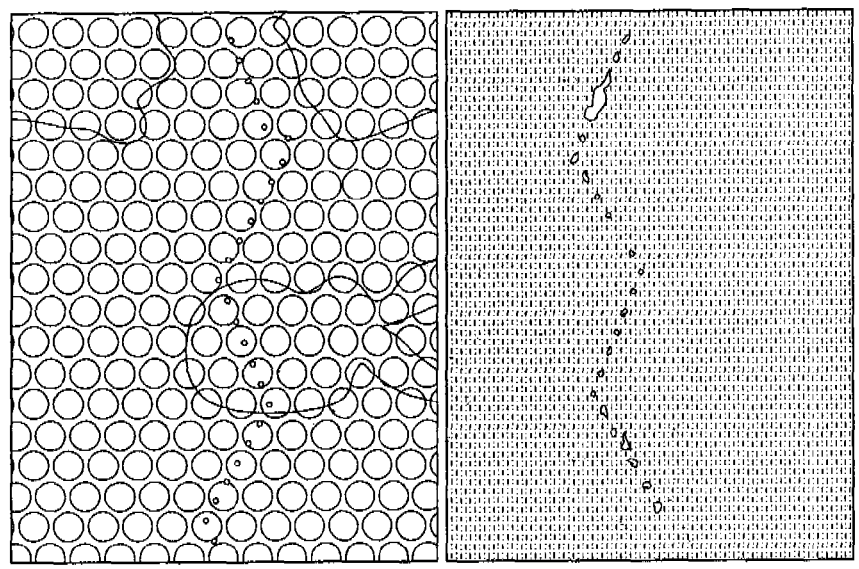

FIG. 20 shows Code 4 (left) and Code 1 (right) after the passive bonds bonding the two materials together were broken. As shown in FIG. 20, Code 1 tore while Code 4 did not. Further, Code 1 contains holes resulting from the breaking of the passive bonds.

Figure 21:
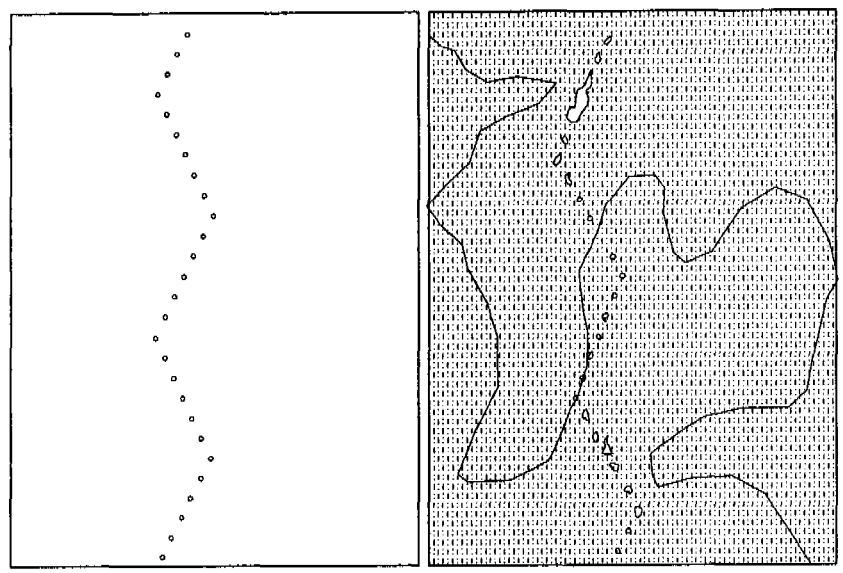

FIG. 21 shows Code 6 (left) and Code 1 (right) after the passive bonds bonding the two materials together were broken. As shown in FIG. 21, Code 1 tore and contains holes resulting from breaking the passive bonds.

Figure 22:
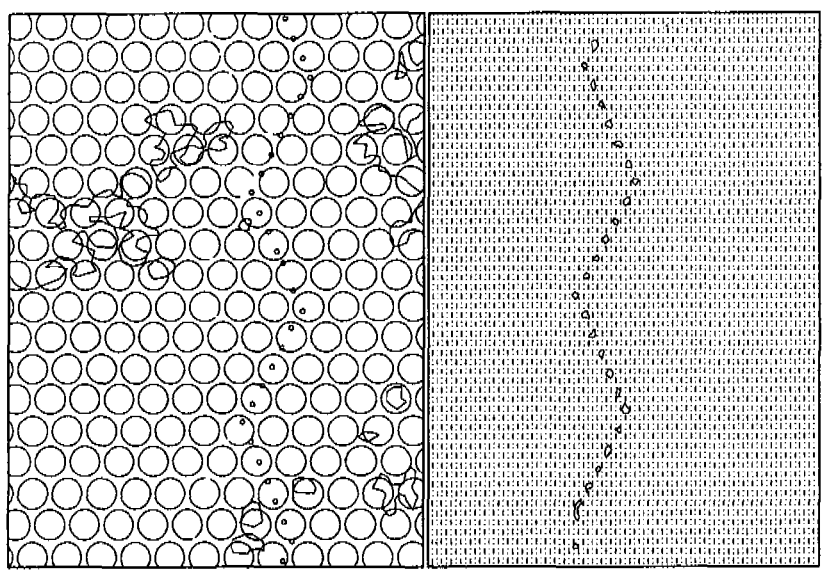

FIG. 22 shows Code 5 (left) and Code 1 (right) after the passive bonds bonding the two materials together were broken. As shown in FIG. 22, Code 1 tore while Code 5 did not.

Figure 23:
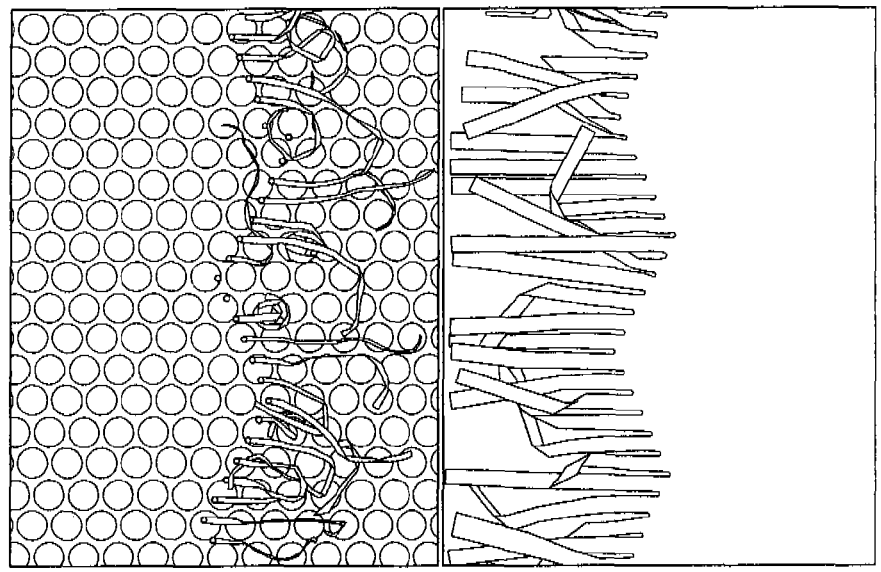

FIG. 23 shows Code 5 (left) and Code 2 (right) after the passive bonds bonding the two materials together were broken. As shown in FIG. 23, Code 2 tore while Code 5 did not.

Figure 24:
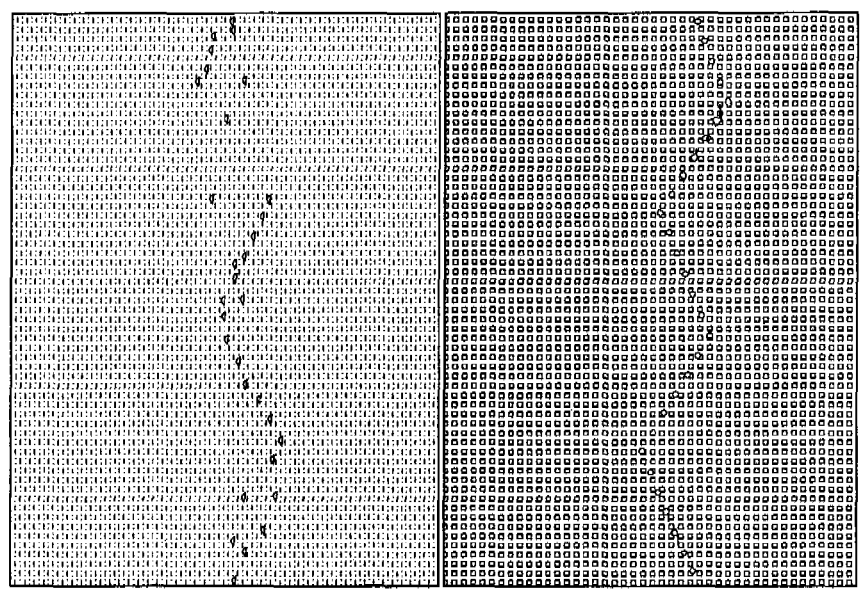

FIG. 24 shows Code 1 (left) and Code 3 (right) after the passive bonds bonding the two materials together were broken. As shown in FIG. 24, Code 1 and Code 3 contain holes resulting from breaking the passive bonds.

Figure 25:
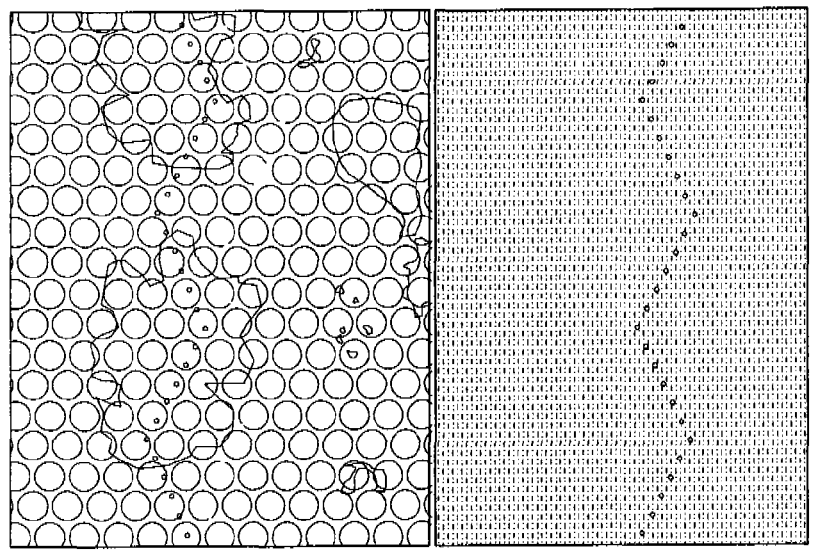

FIG. 25 shows Code 4 (left) and Code 6 (right) after the passive bonds bonding the two materials together were broken. As shown in FIG. 25, Code 4 and Code 6 contain holes resulting from breaking the passive bonds.

Figure 26:
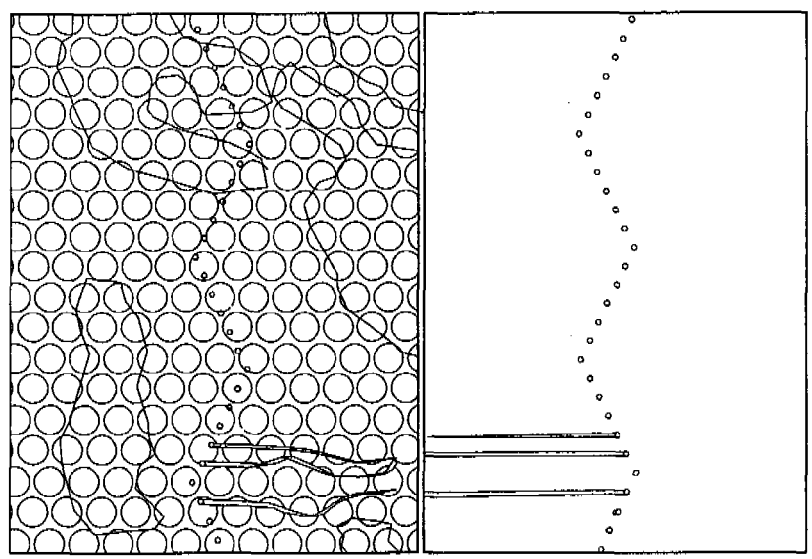

FIG. 26 shows Code 4 (left) and Code 2 (right) after the passive bonds bonding the two materials together were broken. As shown in FIG. 26, Code 2 tore and holes were formed as a result of breaking the passive bonds.

Figure 27:
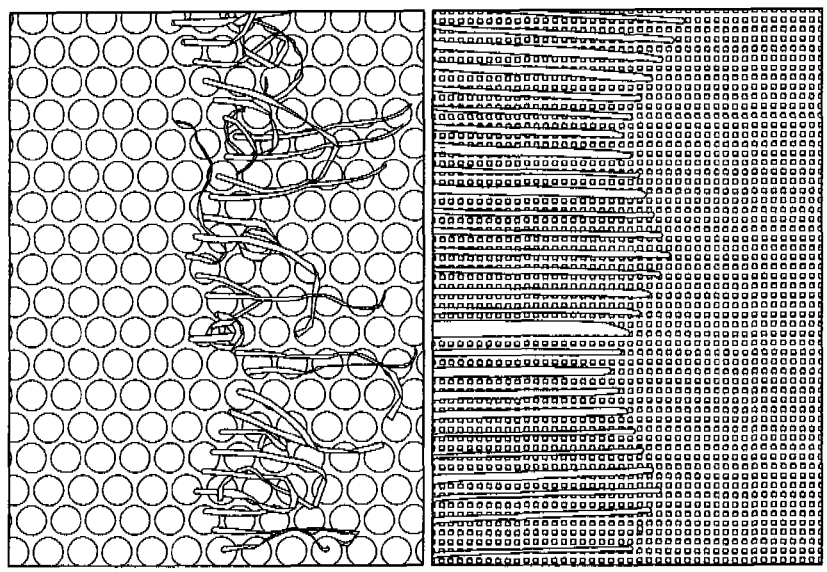

FIG. 27 shows Code 5 (left) and Code 3 (right) after the passive bonds bonding the two materials together were broken. As shown in FIG. 27, Code 3 tore while Code 5 did not.

Separating dissimilar materials connected by ultrasonic passive bonds produces tears in at least one of the materials. Generally, a first material tears more relative to a second material if the first material has a basis weight of less than about 30 gsm and the second material has a basis weight greater than about 30 gsm. Tearing that will impact performance of passive bonds, for example as used in disposable absorbent articles of this invention, can be reduced or prevented by using materials having a basis weight greater than about 30 gsm, and having a first material with a basis weight less than the basis weight of the second material. Although adhesive passive bonds were not generated and tested in this example, results similar to the ultrasonic bonding results can be expected.

Example 3

Several absorbent articles were produced in accordance with the present invention having various passive bonds, as shown in Table 4 below. Bond settings were varied during the passive bonding procedures to determine the effects on the strength of the resulting passive bonds. Several passive bond patterns were tested including the zig-zag bond pattern and the arcuate or curved bond pattern.

Additionally, various bond patterns having different pin diameters and various pin pattern configurations were tested for bond strength. The test results are displayed in Table 5, below. The pin diameter, shown in inches in Table 5, and pin configuration provide a greater sheer strength in the cross-machine or lateral direction (CD) than a peel strength in the machine or longitudinal direction (MD), to maintain a pant-like form during use, and provide the passive bond which can be easily opened for use as a diaper rather than a pant. Ultrasonic passive bonds and adhesive passive bonds were tested.

TABLE 4

Peel Data for Sonic Bond Matrix

| Code | 1 | 2 | 3 | 4 | 5 | 6 |
|---|---|---|---|---|---|---|
| Pattern | zig-zag | zig-zag | curve | curve | curve | curve |
| Point Size | 0.4 | 0.4 | 0.4 | 0.4 | 0.4 | 0.4 |
| Gap | 0.0025 | 0.0025 | 0.0025 | 0.0025 | 0.0025 | 0.0025 |
| Power | 25% | 20% | 25% | 20% | 20% | 20% |
| Weld Time | 0.05 | 0.1 | 0.05 | 0.1 | 0.15 | 0.2 |
| Hold Time | 0.1 | 0.1 | 0.1 | 0.1 | 0.1 | 0.1 |
| Pressure | 15 | 15 | 15 | 15 | 15 | 15 |
| Avg. 3 Peaks (grams) | 1856 | 2397 | 807 | 1241 | 1221 | 1332 |
| % cov. | 5.1 | 6 | 28 | 19.6 | 27.6 | 20.4 |
| Avg. Ld. (grams) | 678 | 741 | 590 | 752 | 755 | 734 |
| % cov. | 8.5 | 3.4 | 13.7 | 10.6 | 11.2 | 4.9 |

The above test varied bonder settings (power and weld time) to determine how strength is affected. Two plates were used: the zig-zag pattern (Codes 1 and 2) and the curved pattern (Codes 3-6). The average load values did not change significantly.

TABLE 5

Sheer and Peel Strengths of Passive Bond Patterns

| Code | Shear (CD) | Peel (CD) | Peel (MD) |
|---|---|---|---|
| 0.02 Curve | 2732 | 512 | 147 |
| 0.02 Zig-Zag | 2577 | 460 | 134 |
| 0.03 Curve | 1150 | 445 | 211 |
| 0.03 Zig-Zag | 2408 | 1158 | 233 |
| 0.04 Curve | 2149 | 403 | |
| 0.04 Zig-Zag | 2891 | 1122 | 201 |
| NS9402 closed | 4722 | | 252 |
| NS9402 open | 4819 | 2448 | 280 |
| RT2304 02 | 687 | 185 | 385 |
| RT2304 03 | 1581 | 385 | 391 |
| RT2315 024 | 1998 | 391 | |
| RT2315 03 | 2553 | | 184 |
| RT2315 05 | 3785 | | 142 |
| RT2315 05 closed | 1346 | 413 | |
| RT2715 019 | 1191 | | |
| RT2715 02 | 2999 | 1648 | 284 |
| RT2715 031 | 4081 | | 326 |
| RT2715 05 | 1375 | 898 | 157 |
| RT2715 04 | 4447 | | 497 |

As shown in Table 5, the bond patterns included a zig-zag pattern (FIG. 11) and a curve pattern (FIG. 13) having pin diameters of 0.02, 0.03 and 0.04 inch. Adhesive bonds were also tested, including adhesives available from National Starch ("NS") located in Cincinnati, Ohio, U.S.A., and Rex-tec Huntsman Polymer Corp. ("RT") located in Odessa, Tex., U.S.A., under various trade designations. The adhesive was applied in a generalized pattern using techniques such as hot melt spray applications. Some codes were run through the adhesive machine with the nip "closed," as indicated in Table 5, to add pressure to the materials being bonded to enhance the adhesive bond.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

What is claimed is:

1. An absorbent article comprising:
   a front waist region, a back waist region, and a crotch region extending between the waist regions,
   a first ear panel formed of a first material extending from a first edge portion of the front waist region;
   a second ear panel formed of a second material different from the first material extending from a first edge portion of the back waist region, the second material having a basis weight greater than a basis weight of the first material; and
   at least one manually tearable passive bond connecting the first ear panel and the second ear panel together.

2. The absorbent article of claim 1 wherein the second material has a basis weight of at least about 20 gsm.

3. The absorbent article of claim 1 wherein the first material has a basis weight of less than about 20 gsm.

4. The absorbent article of claim 1 wherein the second material has a basis weight of at least about 30 gsm.

5. The absorbent article of claim 1 wherein the first material and the second material each has a basis weight of at least about 20 gsm.

6. The absorbent article of claim 1 wherein the first material and the second material each has a basis weight of about 30 gsm to about 60 gsm.

7. The absorbent article of claim 1 wherein the second material has a peak load grab tensile strength of about 8.5 lbs. to about 100 lbs.

8. The absorbent article of claim 1 wherein the first ear panel is passively bonded to the second ear panel by one of sonic welding, adhesive bonding, thermal bonding and combinations thereof.

9. The absorbent article of claim 1 wherein the first material comprises a point bonded nonwoven material.

10. The absorbent article of claim 1 wherein the second material comprises a laminate having at least one film layer positioned between two layers of polypropylene spunbond material.

11. The absorbent article of claim 1 wherein each passive bond has a peel strength of less than about 5000 grams.

12. The absorbent article of claim 1 wherein each passive bond has a peel strength of about 1500 grams to about 3000 grams.

13. An absorbent article comprising:
   a front waist region, a back waist region, and a crotch region extending between the waist regions,
   a first ear panel formed of a first material extending from a first edge portion of the front waist region;

a second ear panel formed of a second material different from the first material extending from a first edge portion of the back waist region; and at least one manually tearable passive bond connecting the first ear panel and the second ear panel together, wherein in disconnecting the first ear panel from the second ear panel, the first ear panel is damaged more than the second ear panel.

14. An absorbent article comprising:

a front waist region, a back waist region, and a crotch region extending between the waist regions, a first ear panel formed of a first material extending from a first edge portion of the front waist region;

a second ear panel formed of a second material different from the first material extending from a first edge portion of the back waist region; and at least one manually tearable passive bond connecting the first ear panel and the second ear panel together, wherein the passive bond can be torn without damaging the second ear panel more than the first ear panel.

15. An absorbent article comprising:

a front waist region, a back waist region, and a crotch region extending between the waist regions, a first ear panel formed of a first material extending from a first edge portion of the front waist region;

a second ear panel formed of a second material different from the first material extending from a first edge portion of the back waist region; and at least one manually tearable passive bond connecting the first ear panel and the second ear panel together, wherein the first ear panel can be disconnected from the second ear panel without negatively affecting a tensile strength of the second ear panel.

16. An absorbent article comprising:

a front waist region, a back waist region, and a crotch region extending between the waist regions, a first ear panel formed of a first material extending from a first edge portion of the front waist region;

a second ear panel formed of a second material different from the first material extending from a first edge portion of the back waist region; and at least one manually tearable passive bond connecting the first ear panel and the second ear panel together, wherein the first ear panel can be disconnected from the second ear panel without negatively affecting a tensile strength of the first ear panel.

* * * * *

UNITED STATES PATENT AND TRADEMARK OFFICE
CERTIFICATE OF CORRECTION

PATENT NO. : 7,473,818 B2  Page 1 of 1
APPLICATION NO. : 10/010965
DATED : January 6, 2009
INVENTOR(S) : Datta et al.

It is certified that error appears in the above-identified patent and that said Letters Patent is hereby corrected as shown below:

Column 4, line 50, between "affecting its" and "strength", insert -- tensile --.

Column 8, line 44, delete "Bermadin", and insert therefor -- Bernardin --.

Column 19, line 46, between "material" and "from", insert -- different --.

Column 20, line 32, between "results" and "displayed", insert -- are --.

Signed and Sealed this

Twenty-fourth Day of March, 2009

JOHN DOLL
*Acting Director of the United States Patent and Trademark Office*